US010954173B2

(12) United States Patent
Venkatramesh et al.

(10) Patent No.: US 10,954,173 B2
(45) Date of Patent: Mar. 23, 2021

(54) MICROBIAL COATING OF CONTROLLED-RELEASE FERTILIZERS

(71) Applicants: AMVAC Chemical Corporation, Newport Beach, CA (US); Pursell Agri-Tech, LLC, Sylacauga, AL (US)

(72) Inventors: Mylavarapu Venkatramesh, Davis, CA (US); Frederic Kendirgi, Davis, CA (US); Spencer Daniel Sanders, Birmingham, AL (US); Allen Zorn Sanders, Sylacauga, AL (US); Murray Paul Hasinoff, Birmingham, AL (US); James Taylor Pursell, Jr., Mountain Brook, AL (US)

(73) Assignees: AMVAC Chemical Corporation, Newport Beach, CA (US); Pursell Agri-Tech, LLC, Sylacauga, AL (US)

( * ) Notice: Subject to any disclaimer, the term of this patent is extended or adjusted under 35 U.S.C. 154(b) by 0 days.

(21) Appl. No.: 16/784,812

(22) Filed: Feb. 7, 2020

(65) Prior Publication Data

US 2020/0255355 A1 Aug. 13, 2020

Related U.S. Application Data

(60) Provisional application No. 62/803,062, filed on Feb. 8, 2019.

(51) Int. Cl.
*C05G 5/30* (2020.01)
*C05C 9/00* (2006.01)
(Continued)

(52) U.S. Cl.
CPC .................. *C05G 5/38* (2020.02); *C05B 7/00* (2013.01); *C05C 1/00* (2013.01); *C05C 3/005* (2013.01);
(Continued)

(58) Field of Classification Search
None
See application file for complete search history.

(56) References Cited

U.S. PATENT DOCUMENTS 5,578,486 A 11/1996 Zhang
9,249,061 B2 2/2016 Harman et al.
(Continued)

FOREIGN PATENT DOCUMENTS

RU 2241692 12/2004
RU 2512277 4/2014

OTHER PUBLICATIONS

Erkovan et al., "Effects of Phosphorus Fertilizer and Phosphorus Solubilizing Bacteria Application on Clover Dominant Meadow: I. Hay Yield and Botanical Composition," *Turkish Journal of Field Crops*, vol. 15, No. 1, pp. 12-17, 2010.
(Continued)

*Primary Examiner* — Wayne A Langel
(74) *Attorney, Agent, or Firm* — Klarquist Sparkman, LLP

(57) ABSTRACT

Compositions including a core particle including at least one fertilizer nutrient and a shell substantially covering the core particle, wherein the shell includes at least one polymer layer or wax layer and one or more species of microbes (such as a population of cells from at least one species of microbes) are provided. In some embodiments, at least one of the polymer layer and/or the wax layer includes the one or more species of microbes. In other examples, the one or more species of microbes are included between layers, for example, between two polymer layers, between two wax layers, or between a polymer layer and a wax layer. Methods of preparing the compositions are also provided. Methods of using the disclosed compositions that include contacting soil, plants, plant parts, or seeds with the composition are provided.

20 Claims, 1 Drawing Sheet

Specification includes a Sequence Listing.

(51) Int. Cl.

| | |
|---|---|
| ***C05B 7/00*** | (2006.01) |
| ***C05C 1/00*** | (2006.01) |
| ***C05C 3/00*** | (2006.01) |
| ***C05C 5/00*** | (2006.01) |
| ***C05D 1/00*** | (2006.01) |
| ***C12N 1/20*** | (2006.01) |

(52) U.S. Cl.
CPC .............. *C05C 5/005* (2013.01); *C05C 9/005* (2013.01); *C05D 1/005* (2013.01); *C05G 5/37* (2020.02); *C12N 1/20* (2013.01)

(56) References Cited

U.S. PATENT DOCUMENTS

| | | | | |
|---|---|---|---|---|
| 9,296,661 | B1 | 3/2016 | Ankeny | |
| 2002/0098982 | A1* | 7/2002 | Burnham ................. | C05D 9/02 504/359 |
| 2007/0131009 | A1* | 6/2007 | Westbrook .............. | C05F 11/08 71/6 |
| 2014/0323297 | A1* | 10/2014 | Harman .................. | C12R 1/885 504/101 |
| 2014/0352376 | A1* | 12/2014 | Carpenter ................ | C05G 5/30 71/6 |
| 2015/0376077 | A1* | 12/2015 | Barr ......................... | C05G 5/38 71/28 |
| 2016/0244378 | A1* | 8/2016 | Tyler ........................ | C05G 3/60 |
| 2019/0183131 | A1 | 6/2019 | Kendirgi et al. | |
| 2019/0256431 | A1* | 8/2019 | Zaseybida ............ | A23K 20/158 |
| 2020/0148605 | A1* | 5/2020 | Burnham ................ | C05F 11/08 |

OTHER PUBLICATIONS

Latha et al., "Effect of Microbial and Chemical Fertilizer on Egg Plant (*Solanum melongena* LINN.) *C. Var* CO-2," *Int. J. Pure. App. Biosci.*, vol. 2, No. 4, pp. 119-124, 2014.

Shaheen et al., "The Integrated Use of Bio-inoculants and Chemical Nitrogen Fertilizer on Growth, Yield and Nutritive Value of Two Okra (*Abelmoschus Esculentus*, L.).Cultivars," *Australian Journal of Basic and Applied Sciences*, vol. 1, No. 3, pp. 307-312, 2007.

* cited by examiner

SEQUENCE LISTING

<160> NUMBER OF SEQ ID NOS: 22

<210> SEQ ID NO 1
<211> LENGTH: 1549
<212> TYPE: DNA
<213> ORGANISM: Bacillus megaterium

<400> SEQUENCE: 1

```
tcggagagtt tgatcctggc tcaggatgaa cgctggcggc gtgcctaata catgcaagtc     60
gagcgaactg attagaagct tgcttctatg acgttagcgg cggacgggtg agtaacacgt    120
gggcaacctg cctgtaagac tgggataact tcgggaaacc gaagctaata ccggatagga    180
tcttctcctt catgggagat gattgaaaga tggtttcggc tatcacttac agatgggccc    240
gcggtgcatt agctagttgg tgaggtaacg gctcaccaag gcaacgatgc atagccgacc    300
tgagagggtg atcggccaca ctgggactga gacacggccc agactcctac gggaggcagc    360
agtagggaat cttccgcaat ggacgaaagt ctgacggagc aacgccgcgt gagtgatgaa    420
ggctttcggg tcgtaaaact ctgttgttag ggaagaacaa gtacgagagt aactgctcgt    480
accttgacgg tacctaacca gaaagccacg gctaactacg tgccagcagc cgcggtaata    540
cgtaggtggc aagcgttatc cggaattatt gggcgtaaag cgcgcgcagg cggtttctta    600
agtctgatgt gaaagcccac ggctcaaccg tggagggtca ttggaaactg gggaacttga    660
gtgcagaaga gaaaagcgga attccacgtg tagcggtgaa atgcgtagag atgtggagga    720
acaccagtgg cgaaggcggc tttttggtct gtaactgacg ctgaggcgcg aaagcgtggg    780
gagcaaacag gattagatac cctggtagtc cacgccgtaa acgatgagtg ctaagtgtta    840
gagggtttcc gccctttagt gctgcagcta acgcattaag cactccgcct ggggagtacg    900
gtcgcaagac tgaaactcaa aggaattgac gggggcccgc acaagcggtg gagcatgtgg    960
tttaattcga agcaacgcga agaaccttac caggtcttga catcctctga caactctaga   1020
gatagagcgt tccccttcgg gggacagagt gacaggtggt gcatggttgt cgtcagctcg   1080
tgtcgtgaga tgttgggtta agtcccgcaa cgagcgcaac ccttgatctt agttgccagc   1140
atttagttgg gcactctaag gtgactgccg gtgacaaacc ggaggaaggt ggggatgacg   1200
tcaaatcatc atgcccctta tgacctgggc tacacacgtg ctacaatgga tggtacaaag   1260
ggctgcaaga ccgcgaggtc aagccaatcc cataaaacca ttctcagttc ggattgtagg   1320
ctgcaactcg cctacatgaa gctggaatcg ctagtaatcg cggatcagca tgccgcggtg   1380
aatacgttcc cgggccttgt acacaccgcc cgtcacacca cgagagtttg taacacccga   1440
agtcggtgga gtaaccgtaa ggagctagcc gcctaaggtg ggacagatga ttggggtgaa   1500
gtcgtaacaa ggtagccgta tcggaaggtg cggctggatc acctcctttt               1549
```

<210> SEQ ID NO 2
<211> LENGTH: 1567
<212> TYPE: DNA
<213> ORGANISM: Lactobacillus casei/paracasei

<400> SEQUENCE: 2

```
tatgagagtt tgatcctggc tcaggatgaa cgctggcggc gtgcctaata catgcaagtc     60
gaacgagttc tcgttgatga tcggtgcttg caccgagatt caacatggaa cgagtggcgg    120
acgggtgagt aacacgtggg taacctgccc ttaagtgggg gataacattt ggaaacagat    180
gctaataccg catagatcca agaaccgcat ggttcttggc tgaaagatgg cgtaagctat    240
cgcttttgga tggacccgcg gcgtattagc tagttggtga ggtaacggct caccaaggcg    300
```

-continued

```
atgatacgta gccgaactga gaggttgatc ggccacattg ggactgagac acggcccaaa    360
ctcctacggg aggcagcagt agggaatctt ccacaatgga cgcaagtctg atggagcaac    420
gccgcgtgag tgaagaaggc tttcgggtcg taaaactctg ttgttggaga agaatggtcg    480
gcagagtaac tgttgtcggc gtgacggtat ccaaccagaa agccacggct aactacgtgc    540
cagcagccgc ggtaatacgt aggtggcaag cgttatccgg atttattggg cgtaaagcga    600
gcgcaggcgg tttttttaagt ctgatgtgaa agccctcggc ttaaccgagg aagcgcatcg    660
gaaactggga aacttgagtg cagaagagga cagtggaact ccatgtgtag cggtgaaatg    720
cgtagatata tggaagaaca ccagtggcga aggcggctgt ctggtctgta actgacgctg    780
aggctcgaaa gcatgggtag cgaacaggat tagataccct ggtagtccat gccgtaaacg    840
atgaatgcta ggtgttggag ggtttccgcc cttcagtgcc gcagctaacg cattaagcat    900
tccgcctggg gagtacgacc gcaaggttga aactcaaagg aattgacggg ggcccgcaca    960
agcggtggag catgtggttt aattcgaagc aacgcgaaga accttaccag gtcttgacat   1020
cttttgatca cctgagagat caggtttccc cttcgggggc aaaatgacag gtggtgcatg   1080
gttgtcgtca gctcgtgtcg tgagatgttg ggttaagtcc cgcaacgagc gcaaccctta   1140
tgactagttg ccagcattta gttgggcact ctagtaagac tgccggtgac aaaccggagg   1200
aaggtgggga tgacgtcaaa tcatcatgcc ccttatgacc tgggctacac acgtgctaca   1260
atggatggta caacgagttg cgagaccgcg aggtcaagct aatctcttaa agccattctc   1320
agttcggact gtaggctgca actcgcctac acgaagtcgg aatcgctagt aatcgcggat   1380
cagcacgccg cggtgaatac gttcccgggc cttgtacaca ccgcccgtca caccatgaga   1440
gtttgtaaca cccgaagccg gtggcgtaac ccttttaggg agcgagccgt ctaaggtggg   1500
acaaatgatt agggtgaagt cgtaacaagg tagccgtagg agaacctgcg gctggatcac   1560
ctccttt                                                             1567
```

<210> SEQ ID NO 3
<211> LENGTH: 1510
<212> TYPE: DNA
<213> ORGANISM: Clostridium beijerinckii

<400> SEQUENCE: 3

```
tattgagagt ttgatcctgg ctcaggacga acgctggcgg cgtgcttaac acatgcaagt     60
cgagcgatga agttccttcg ggaatggatt agcggcggac gggtgagtaa cacgtgggta    120
acctgcctca tagaggggaa tagcctttcg aaaggaagat taataccgca taagattgta    180
gtgccgcatg gcatagcaat taaaggagta atccgctatg agatggaccc gcgtcgcatt    240
agctagttgg tgaggtaacg gctcaccaag gcgacgatgc gtagccgacc tgagagggtg    300
atcggccaca ttgggactga gacacggccc agactcctac gggaggcagc agtggggaat    360
attgcacaat gggggaaacc ctgatgcagc aacgccgcgt gagtgatgac ggtcttcgga    420
ttgtaaagct ctgtcttcag ggacgataat gacggtacct gaggaggaag ccacggctaa    480
ctacgtgcca gcagccgcgg taatacgtag gtggcaagcg ttgtccggat ttactgggcg    540
taaagggagc gtaggtggat atttaagtgg gatgtgaaat actcgggctt aacctgggtg    600
ctgcattcca aactggatat ctagagtgca ggagaggaaa gtagaattcc tagtgtagcg    660
gtgaaatgcg tagagattag gaagaatacc agtggcgaag gcgactttct ggactgtaac    720
tgacactgag gctcgaaagc gtggggagca aacaggatta gataccctgg tagtccacgc    780
cgtaaacgat gaatactagg tgtaggggtt gtcatgacct ctgtgccgcc gctaacgcat    840
```

-continued

```
taagtattcc gcctggggag tacggtcgca agattaaaac tcaaaggaat tgacgggggc     900

ccgcacaagc agcggagcat gtggtttaat tcgaagcaac gcgaagaacc ttacctagac     960

ttgacatctc ctgaattacc cttaatcggg gaagcccttc ggggcaggaa gacaggtggt    1020

gcatggttgt cgtcagctcg tgtcgtgaga tgttgggtta agtcccgcaa cgagcgcaac    1080

ccttattgtt agttgctacc atttagttga gcactctagc gagactgccc gggttaaccg    1140

ggaggaaggt ggggatgacg tcaaatcatc atgcccctta tgtctagggc tacacacgtg    1200

ctacaatggc tggtacagag agatgctaaa ccgtgaggtg gagccaaact ttaaaaccag    1260

tctcagttcg gattgtaggc tgaaactcgc ctacatgaag ctggagttgc tagtaatcgc    1320

gaatcagaat gtcgcggtga atacgttccc gggccttgta cacaccgccc gtcacaccat    1380

gagagttggc aatacccaaa gttcgtgagc taacgcgcaa gcggggcagc gacctaaggt    1440

agggtcagcg attggggtga agtcgtaaca aggtagccgt aggagaacct gcggctggat    1500

cacctccttt                                                           1510
```

<210> SEQ ID NO 4
<211> LENGTH: 1485
<212> TYPE: DNA
<213> ORGANISM: Acetobacter pasteurianus

<400> SEQUENCE: 4

```
cctgagagtt tgatcctggc tcagagcgaa cgctggcggc atgcttaaca catgcaagtc      60

gcacgaaggt ttcggcctta gtggcggacg ggtgagtaac gcgtaggtat ctatccatgg     120

gtgggggata acactgggaa actggtgcta ataccgcatg acacctgagg gtcaaaggcg     180

caagtcgcct gtggaggagc ctgcgtttga ttagctagtt ggtggggtaa aggcctacca     240

aggcgatgat caatagctgg tttgagagga tgatcagcca cactgggact gagacacggc     300

ccagactcct acgggaggca gcagtgggga atattggaca atgggggcaa ccctgatcca     360

gcaatgccgc gtgtgtgaag aaggtcttcg gattgtaaag cactttcgac ggggacgatg     420

atgacggtac ccgtagaaga agccccggct aacttcgtgc cagcagccgc ggtaatacga     480

agggggctag cgttgctcgg aatgactggg cgtaaagggc gtgtaggcgg tttgtacagt     540

cagatgtgaa atccccgggc ttaacctggg agctgcattt gatacgtgca gactagagtg     600

tgagagaggg ttgtggaatt cccagtgtag aggtgaaatt cgtagatatt gggaagaaca     660

ccggtggcga aggcggcaac ctggctcatt actgacgctg aggcgcgaaa gcgtggggag     720

caaacaggat tagataccct ggtagtccac gctgtaaacg atgtgtgcta gatgttgggt     780

gacttagtca ttcagtgtcg cagttaacgc gttaagcaca ccgcctgggg agtacggccg     840

caaggttgaa actcaaagga attgacgggg gcccgcacaa gcggtggagc atgtggttta     900

attcgaagca acgcgcagaa ccttaccagg gcttgaatgt agaggctgca agcagagatg     960

tttgtttccc gcaagggacc tctaacacag gtgctgcatg gctgtcgtca gctcgtgtcg    1020

tgagatgttg ggttaagtcc cgcaacgagc gcaaccccta tctttagttg ccatcaggtt    1080

gggctgggca ctctagagag actgccggtg acaagccgga ggaaggtggg gatgacgtca    1140

agtcctcatg gcccttatgt cctgggctac acacgtgcta caatggcggt gacagtggga    1200

agctaggtgg tgacaccatg ctgatctcta aaagccgtct cagttcggat tgcactctgc    1260

aactcgagtg catgaaggtg gaatcgctag taatcgcgga tcagcatgcc gcggtgaata    1320

cgttcccggg ccttgtacac accgcccgtc acaccatggg agttggtttg accttaagcc    1380
```

-continued ggtgagcgaa ccgcaaggac gcagccgacc acggtcgggt cagcgactgg ggtgaagtcg 1440
taacaaggta gccgtagggg aacctgcggc tggatcacct ccttt 1485

<210> SEQ ID NO 5
<211> LENGTH: 1571
<212> TYPE: DNA
<213> ORGANISM: Lactobacillus buchneri

<400> SEQUENCE: 5
atgagagttt gatcctggct caggacgaac gctggcggcg tgcctaatac atgcaagtcg 60
aacgcgtctc cgttaatgat tttaggtgct tgcacttgaa agatttaaca ttgagacgag 120
tggcgaactg gtgagtaaca cgtgggtaac ctgcccttga agtaggggat aacacttgga 180
aacaggtgct aataccgtat aacaaccaaa accacctggt tttggtttaa aagacggctt 240
cggctgtcac tttaggatgg acccgcggcg tattagcttg ttggtaaggt aacggcctac 300
caaggcgatg atacgtagcc gacctgagag ggtaatcggc cacattggga ctgagacacg 360
gcccaaactc ctacgggagg cagcagtagg gaatcttcca caatggacga aagtctgatg 420
gagcaacgcc gcgtgagtga tgaagggttt cggctcgtaa aactctgttg ttggagaaga 480
acaggtgtca gagtaactgt tgacatcttg acggtatcca accagaaagc cacggctaac 540
tacgtgccag cagccgcggt aatacgtagg tggcaagcgt tgtccggatt tattgggcgt 600
aaagcgagcg caggcggttt tttaggtctg atgtgaaagc cttcggctta accggagaag 660
tgcatcggaa accgggagac ttgagtgcag aagaggacag tggaactcca tgtgtagcgg 720
tgaaatgcgt agatatatgg aagaacacca gtggcgaagg cggctgtctg gtctgtaact 780
gacgctgagg ctcgaaagca tgggtagcga acaggattag ataccctggt agtccatgcc 840
gtaaacgatg agtgctaagt gttggagggt ttccgccctt cagtgctgca gctaacgcat 900
taagcactcc gcctggggag tacgaccgca aggttgaaac tcaaaggaat tgacgggggc 960
ccgcacaagc ggtggagcat gtggtttaat tcgatgctac gcgaagaacc ttaccaggtc 1020
ttgacatctt ctgccaactt aagagattag gcgttccctt cggggacaga atgacaggtg 1080
gtgcatggtt gtcgtcagct cgtgtcgtga gatgttgggt taagtcccgc aacgagcgca 1140
acccttattg ttagttgcca gcattcagtt gggcactcta gcaagactgc cggtgacaaa 1200
ccggaggaag gtggggatga cgtcaaatca tcatgcccct tatgacctgg gctacacacg 1260
tgctacaatg gacggtacaa cgagtcgcga aaccgcgagg tcaagctaat ctcttaaagc 1320
cgttctcagt tcggattgta ggctgcaact cgcctacatg aagttggaat cgctagtaat 1380
cgtggatcag catgccacgg tgaatacgtt cccgggcctt gtacacaccg cccgtcacac 1440
catgagagtt tgtaacaccc aaagccggtg aggtaacctt cggggaccag ccgtctaagg 1500
tggggcagat gattagggtg aagtcgtaac aaggtagccg taggagaacc tgcggctgga 1560
tcacctcctt t 1571

<210> SEQ ID NO 6
<211> LENGTH: 1548
<212> TYPE: DNA
<213> ORGANISM: Bacillus subtilis

<400> SEQUENCE: 6
atcggagagt ttgatcctgg ctcaggacga acgctggcgg cgtgcctaat acatgcaagt 60
cgagcggaca gatgggagct tgctccctga tgttagcggc ggacgggtga gtaacacgtg 120
ggtaacctgc ctgtaagact gggataactc cgggaaaccg gggctaatac cggatggttg 180

-continued

```
tttgaaccgc atggttcaaa cataaaaggt ggcttcggct accacttaca gatggacccg    240
cggcgcatta gctagttggt gaggtaacgg ctcaccaagg caacgatgcg tagccgacct    300
gagagggtga tcggccacac tgggactgag acacggccca gactcctacg ggaggcagca    360
gtagggaatc ttccgcaatg gacgaaagtc tgacggagca acgccgcgtg agtgatgaag    420
gttttcggat cgtaaagctc tgttgttagg gaagaacaag taccgttcga atagggcggt    480
accttgacgg tacctaacca gaaagccacg gctaactacg tgccagcagc cgcggtaata    540
cgtaggtggc aagcgttgtc cggaattatt gggcgtaaag ggctcgcagg cggtttctta    600
agtctgatgt gaaagccccc ggctcaaccg ggagggtca ttggaaactg ggaacttga    660
gtgcagaaga ggagagtgga attccacgtg tagcggtgaa atgcgtagag atgtggagga    720
acaccagtgg cgaaggcgac tctctggtct gtaactgacg ctgaggagcg aaagcgtggg    780
gagcgaacag gattagatac cctggtagtc cacgccgtaa acgatgagtg ctaagtgtta    840
gggggtttcc gccccttagt gctgcagcta acgcattaag cactccgcct ggggagtacg    900
gtcgcaagac tgaaactcaa aggaattgac gggggcccgc acaagcggtg gagcatgtgg    960
tttaattcga agcaacgcga agaaccttac caggtcttga catcctctga caatcctaga   1020
gataggacgt ccccttcggg ggcagagtga caggtggtgc atggttgtcg tcagctcgtg   1080
tcgtgagatg ttgggttaag tcccgcaacg agcgcaaccc ttgatcttag ttgccagcat   1140
tcagttgggc actctaaggt gactgccggt gacaaaccgg aggaaggtgg ggatgacgtc   1200
aaatcatcat gccccttatg acctgggcta cacacgtgct acaatggaca gaacaaaggg   1260
cagcgaaacc gcgaggttaa gccaatccca caaatctgtt ctcagttcgg atcgcagtct   1320
gcaactcgac tgcgtgaagc tggaatcgct agtaatcgcg gatcagcatg ccgcggtgaa   1380
tacgttcccg ggccttgtac acaccgcccg tcacaccacg agagtttgta acacccgaag   1440
tcggtgaggt aacctttag gagccagccg ccgaaggtgg gacagatgat tggggtgaag   1500
tcgtaacaag gtagccgtat cggaaggtgc ggctggatca cctccttt                1548
```

<210> SEQ ID NO 7
<211> LENGTH: 1552
<212> TYPE: DNA
<213> ORGANISM: Paenibacillus cookii

<400> SEQUENCE: 7

```
cttggagagt ttgatcctgg ctcaggacga acgctggcgg cgtgcctaat acatgcaagt     60
cgagcggagt tgatggggag cttgctctcc tgagacttag cggcggacgg gtgagtaaca    120
cgtaggcaac ctgcccgtaa gaccgggata actaccggaa acggtagcta ataccggata    180
atttatcgct tcgcatggag cggtaatgaa agacggagca atctgtcact tacggatggg    240
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc cagggaagaa cgtcgggtag agtaactgct    480
atccgagtga cggtacctga gaagaaagcc ccggctaact acgtgccagc agccgcggta    540
atacgtaggg ggcaagcgtt gtccggaatt attgggcgta aagcgcgcgc aggcggtcac    600
ttaagtctgg tgtttaaggc tagggctcaa ctctagttcg cactggaaac tgggtgactt    660
gagtgcagaa gaggaaagtg gaattccacg tgtagcggtg aaatgcgtag agatgtggag    720
gaacaccagt ggcgaaggcg actttctggg ctgtaactga cgctgaggcg cgaaagcgtg    780
```

-continued

```
gggagcaaac aggattagat accctggtag tccacgccgt aaacgatgaa tgctaggtgt     840

taggggtttc gatacccttg gtgccgaagt taacacatta agcattccgc ctggggagta     900

cggtcgcaag actgaaactc aaaggaattg acggggaccc gcacaagcag tggagtatgt     960

ggtttaattc gaagcaacgc gaagaacctt accaggtctt gacatccctc tgaatcctct    1020

agagatagag gcggccttcg ggacagagga gacaggtggt gcatggttgt cgtcagctcg    1080

tgtcgtgaga tgttgggtta agtcccgcaa cgagcgcaac ccttgatttt agttgccagc    1140

acattaaggt gggcactcta gaatgactgc cggtgacaaa ccggaggaag gcggggatga    1200

cgtcaaatca tcatgcccct tatgacctgg gctacacacg tactacaatg gccagtacaa    1260

cgggaagcga agtcgcgaga cggagccaat cctatcaaag ctggtctcag ttcggattgc    1320

aggctgcaac ccgcctgcat gaagtcggaa ttgctagtaa tcgcggatca gcatgccgcg    1380

gtgaatacgt tcccgggtct tgtacacacc gcccgtcaca ccacgagagt ttacaacacc    1440

cgaagtcggt ggggtaaccg caaggagcca gccgccgaag gtggggtaga tgattggggt    1500

gaagtcgtaa caaggtagcc gtatcggaag gtgcggctgg atcacctcct tt            1552
```

<210> SEQ ID NO 8
<211> LENGTH: 1554
<212> TYPE: DNA
<213> ORGANISM: Lactobacillus vini

<400> SEQUENCE: 8

```
aatgagagtt tgatcctggc tcaggacgaa cgctggcggc gtgcctaata catgcaagtc      60

gaacgagact tttatttga tgcttgcatc ttttaaaaag ttgagtggcg aacgggtgag      120

taacacgtgg gtaacctgcc ttaaagtggg ggataacact tggaaacagg tgctaatacc     180

gcataaccat caaaaccgcc tggttttgat gttaaagatg gttctgctat cgctttaaga     240

tggacccgcg gcgtattagc tagttggtga ggtaacggct taccaaggca atgatacgta     300

gccgaactga gaggttgatc ggccacattg ggactgagac acggcccaaa ctcctacggg     360

aggcagcagt agggaatctt tcacaatgga cgaaagtctg atggagcaac gccgcgtgag     420

tgaagaaggt tttcggatcg taaaactctg ttgtcagaga agaacgtgtg tgagagtaac     480

tgttcacgca gtgacggtat ctgaccagaa agtcacggct aactacgtgc cagcagccgc     540

ggtaatacgt aggtggcaag cgttgtccgg atttattggg cgtaaaggga acgcaggcgg     600

tcttttaagt ctgatgtgaa agccttcggc ttaaccgaag tcgggcattg gaaactggga     660

gacttgagtg cagaagagga gagtggaact ccatgtgtag cggtgaaatg cgtagatata     720

tggaagaaca ccagtggcga aagcggctct ctggtctgta actgacgctg aggttcgaaa     780

gcgtgggtag caaacaggat tagataccct ggtagtccac gccgtaaacg atgaatgcta     840

agtgttggag ggtttccgcc cttcagtgcc gcagctaacg cattaagcat tccgcctggg     900

gagtacgatc gcaagattga aactcaaagg aattgacggg ggcccgcaca agcggtggag     960

catgtggttt aattcgaagc aacgcgaaga accttaccag gtcttgacat cttttgctaa    1020

cctgagagat caggtgttcc cttcggggac aaaatgacag gtggtgcatg gttgtcgtca    1080

gctcgtgtcg tgagatgttg ggttaagtcc cgcaacgagc gcaaccctta ttgttagttg    1140

ccagcattta gttgggcact ctaacgagac tgccggtgac aaaccggagg aaggtgggga    1200

tgacgtcaaa tcatcatgcc ccttatgacc tgggctacac acgtgctaca atggacggta    1260

caacgagtcg caagaccgcg aggtcaagct aatctctgaa aaccgttctc agttcggatt    1320

gcaggctgca actcgcctgc atgaagtcgg aatcgctagt aatcgcggat cagcatgccg    1380
```

-continued cggtgaatac gttcccgggc cttgtacaca ccgcccgtca caccatgaga gtttgtaaca 1440
cccaaagccg gtggggtaac ctttgggagc cagccgtcta aggtgggaca gatgattggg 1500
gtgaagtcgt aacaaggtag ccgtaggaga acctgcggct ggatcacctc cttt 1554

<210> SEQ ID NO 9
<211> LENGTH: 1549
<212> TYPE: DNA
<213> ORGANISM: Bacillus licheniformis

<400> SEQUENCE: 9
catggagagt ttgatcctgg ctcaggacga acgctggcgg cgtgcctaat acatgcaagt 60
cgagcggacc gacgggagct tgctccctta ggtcagcggc ggacgggtga gtaacacgtg 120
ggtaacctgc ctgtaagact gggataactc cgggaaaccg gggctaatac cggatgcttg 180
attgaaccgc atggttccaa tcataaaagg tggcttttag ctaccactta cagatggacc 240
cgcggcgcat tagctagttg gtgaggtaac ggctcaccaa ggcgacgatg cgtagccgac 300
ctgagagggt gatcggccac actgggactg agacacggcc cagactccta cgggaggcag 360
cagtagggaa tcttccgcaa tggacgaaag tctgacggag caacgccgcg tgagtgatga 420
aggttttcgg atcgtaaaac tctgttgtta gggaagaaca agtaccgttc gaatagggcg 480
gcaccttgac ggtacctaac cagaaagcca cggctaacta cgtgccagca gccgcggtaa 540
tacgtaggtg gcaagcgttg tccggaatta ttgggcgtaa agcgcgcgca ggcggtttct 600
taagtctgat gtgaaagccc ccggctcaac cggggagggt cattggaaac tggggaactt 660
gagtgcagaa gaggagagtg gaattccacg tgtagcggtg aaatgcgtag agatgtggag 720
gaacaccagt ggcgaaggcg actctctggt ctgtaactga cgctgaggcg cgaaagcgtg 780
gggagcgaac aggattagat accctggtag tccacgccgt aaacgatgag tgctaagtgt 840
tagagggttt ccgcccttta gtgctgcagc aaacgcatta agcactccgc ctggggagta 900
cggtcgcaag actgaaactc aaaggaattg acgggggccc gcacaagcgg tggagcatgt 960
ggtttaattc gaagcaacgc gaagaacctt accaggtctt gacatcctct gacaacccta 1020
gagatagggc ttccccttcg ggggcagagt gacaggtggt gcatggttgt cgtcagctcg 1080
tgtcgtgaga tgttgggtta agtcccgcaa cgagcgcaac ccttgatctt agttgccagc 1140
attcagttgg gcactctaag gtgactgccg gtgacaaacc ggaggaaggt ggggatgacg 1200
tcaaatcatc atgcccctta tgacctgggc tacacacgtg ctacaatggg cagaacaaag 1260
ggcagcgaag ccgcgaggct aagccaatcc cacaaatctg ttctcagttc ggatcgcagt 1320
ctgcaactcg actgcgtgaa gctggaatcg ctagtaatcg cggatcagca tgccgcggtg 1380
aatacgttcc cgggccttgt acacaccgcc cgtcacacca cgagagtttg taacacccga 1440
agtcggtgag gtaacctttt ggagccagcc gccgaaggtg ggacagatga ttggggtgaa 1500
gtcgtaacaa ggtagccgta tcggaaggtg cggctggatc acctcctttt 1549

<210> SEQ ID NO 10
<211> LENGTH: 1553
<212> TYPE: DNA
<213> ORGANISM: Paenibacillus lautus

<400> SEQUENCE: 10
attggagagt ttgatcctgg ctcaggacga acgctggcgg cgtgcctaat acatgcaagt 60
cgagcggact tgatggagtg cttgcactcc tgaaggttag cggcggacgg gtgagtaaca 120
cgtaggcaac ctgccctcaa gactgggata actaccggaa acggtagcta ataccggata 180

-continued

```
atttattttg cagcattgtg aaataatgaa aggcggagca atctgtcact tgaggatggg    240
cctgcggcgc attagctagt tggtggggta acggcccacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc caaggaagaa cgtcttctag agtaactgct    480
aggagagtga cggtacttga gaagaaagcc ccggctaact acgtgccagc agccgcggta    540
atacgtaggg ggcaagcgtt gtccggaatt attgggcgta aagcgcgcgc aggcggttct    600
ttaagtctgg tgtttaaacc cgaggctcaa cttcgggtcg cactggaaac tggggaactt    660
gagtgcagaa gaggagagtg gaattccacg tgtagcggtg aaatgcgtag atatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
taggggtttc gataccettg gtgccgaagt taacacatta agcattccgc ctggggagta    900
cggtcgcaag actgaaactc aaaggaattg acggggaccc gcacaagcag tggagtatgt    960
ggtttaattc gaagcaacgc gaagaacctt accaagtctt gacatccctc tgaatcctct   1020
agagatagag gcggccttcg ggacagaggt gacaggtggt gcatggttgt cgtcagctcg   1080
tgtcgtgaga tgttgggtta agtcccgcaa cgagcgcaac ccttgatttt agttgccagc   1140
acttcgggtg ggcactctag aatgactgcc ggtgacaaac cggaggaagg cggggatgac   1200
gtcaaatcat catgcccctt atgacttggg ctacacacgt actacaatgg ctggtacaac   1260
gggaagcgaa gccgcgaggt ggagccaatc ctataaaagc cagtctcagt tcggattgca   1320
ggctgcaact cgcctgcatg aagtcggaat tgctagtaat cgcggatcag catgccgcgg   1380
tgaatacgtt cccgggtctt gtacacaccg cccgtcacac cacgagagtt tacaacaccc   1440
gaagtcggtg gggtaaccct taggggagcc agccgccgaa ggtggggtag atgattgggg   1500
tgaagtcgta acaaggtagc cgtatcggaa ggtgcggctg gatcacctcc ttt          1553
```

```
<210> SEQ ID NO 11
<211> LENGTH: 1561
<212> TYPE: DNA
<213> ORGANISM: Oceanobacillus oncorhynchi

<400> SEQUENCE: 11

ttatggagag tttgatcttg gctcaggacg aacgctggcg gcgtgcctaa tacatgcaag     60
tcgagcgcgg gaagcgaacg gaactcttcg gagggaagtt cgtggaacga gcggcggacg    120
ggtgagtaac acgtaggcaa cctgcctgta agactgggat aactcgcgga aacgcgagct    180
aataccggat aacactttct atcacctgat ggaaagttga aaggcggctt ttgctgtcac    240
ttacagatgg gcctgcggcg cattagctag ttggtgaggt aacggctcac caaggcgacg    300
atgcgtagcc gacctgagag ggtgatcggc cacactggga ctgagacacg gcccagactc    360
ctacgggagg cagcagtagg gaatcttccg caatggacga aagtctgacg gagcaacgcc    420
gcgtgagtga tgaaggtttt cggatcgtaa aactctgttg tcagggaaga acaagtacga    480
tagtaactga tcgtaccttg acggtacctg accagaaagc cacggctaac tacgtgccag    540
cagccgcggt aatacgtagg tggcaagcgt tgtccggaat tattgggcgt aaagcgctcg    600
caggcggttc tttaagtctg atgtgaaatc ttgcggctca accgcaaacg tgcattggaa    660
actggaggac ttgagtgcag aagaggagag tggaattcca cgtgtagcgg tgaaatgcgt    720
agagatgtgg aggaacacca gtggcgaagg cgactctctg gtctgtaact gacgctgagg    780
```

-continued agcgaaagcg tggggagcga acaggattag ataccctggt agtccacgcc gtaaacgatg 840
agtgctaggt gttagggggt ttccgcccct tagtgctgaa gttaacgcat taagcactcc 900
gcctggggag tacggccgca aggctgaaac tcaaaagaat tgacggggac ccgcacaagc 960
ggtggagcat gtggtttaat tcgaagcaac gcgaagaacc ttaccaggtc ttgacatcct 1020
ttgaccgctc tagagataga gttttccctt cggggacaaa gtgacaggtg gtgcatggtt 1080
gtcgtcagct cgtgtcgtga gatgttgggt taagtcccgc aacgagcgca acccttaatc 1140
ttagttgcca gcatttagtt gggcactcta aggtgactgc cggtgacaaa ccggaggaag 1200
gtggggatga cgtcaaatca tcatgcccct tatgacctgg gctacacacg tgctacaatg 1260
gacggaacaa agggaagcga acccgcgagg tccagcaaat cccataaaac cgttctcagt 1320
tcggattgca ggctgcaact cgcctgcatg aagccggaat cgctagtaat cgcggatcag 1380
catgccgcgg tgaatacgtt cccgggtctt gtacacaccg cccgtcacac cacgagagtt 1440
cgtaacaccc gaagtcggtg aggtaacctt ttggagccag ccgccgaagg tgggacgaat 1500
gattggggtg aagtcgtaac aaggtagccg tatcggaagg tgcggctgga tcacctcctt 1560
t 1561

<210> SEQ ID NO 12
<211> LENGTH: 1548
<212> TYPE: DNA
<213> ORGANISM: Bacillus amyloliquefaciens

<400> SEQUENCE: 12
atcggagagt ttgatcctgg ctcaggacga acgctggcgg cgtgcctaat acatgcaagt 60
cgagcggaca gatgggagct tgctccctga tgttagcggc ggacgggtga gtaacacgtg 120
ggtaacctgc ctgtaagact gggataactc cgggaaaccg gggctaatac cggatggttg 180
tctgaaccgc atggttcaga cataaaaggt ggcttcggct accacttaca gatggacccg 240
cggcgcatta gctagttggt gaggtaacgg ctcaccaagg cgacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gttttcggat cgtaaagctc tgttgttagg gaagaacaag tgccgttcaa atagggcggc 480
accttgacgg tacctaacca gaaagccacg gctaactacg tgccagcagc cgcggtaata 540
cgtaggtggc aagcgttgtc cggaattatt gggcgtaaag ggctcgcagg cggtttctta 600
agtctgatgt gaaagccccc ggctcaaccg gggagggtca ttggaaactg gggaacttga 660
gtgcagaaga ggagagtgga attccacgtg tagcggtgaa atgcgtagag atgtggagga 720
acaccagtgg cgaaggcgac tctctggtct gtaactgacg ctgaggagcg aaagcgtggg 780
gagcgaacag gattagatac cctggtagtc cacgccgtaa acgatgagtg ctaagtgtta 840
gggggtttcc gccccttagt gctgcagcta acgcattaag cactccgcct ggggagtacg 900
gtcgcaagac tgaaactcaa aggaattgac gggggcccgc acaagcggtg gagcatgtgg 960
tttaattcga agcaacgcga agaaccttac caggtcttga catcctctga caatcctaga 1020
gataggacgt ccccttcggg ggcagagtga caggtggtgc atggttgtcg tcagctcgtg 1080
tcgtgagatg ttgggttaag tcccgcaacg agcgcaaccc ttgatcttag ttgccagcat 1140
tcagttgggc actctaaggt gactgccggt gacaaaccgg aggaaggtgg ggatgacgtc 1200
aaatcatcat gccccttatg acctgggcta cacacgtgct acaatggaca gaacaaaggg 1260
cagcgaaacc gcgaggttaa gccaatccca caaatctgtt ctcagttcgg atcgcagtct 1320
gcaactcgac tgcgtgaagc tggaatcgct agtaatcgcg gatcagcatg ccgcggtgaa 1380
tacgttcccg ggccttgtac acaccgcccg tcacaccacg agagtttgta acacccgaag 1440
tcggtgaggt aacctttatg gagccagccg ccgaaggtgg gacagatgat tggggtgaag 1500
tcgtaacaag gtagccgtat cggaaggtgc ggctggatca cctccttt 1548

<210> SEQ ID NO 13
<211> LENGTH: 1547
<212> TYPE: DNA
<213> ORGANISM: Bacillus sp.

<400> SEQUENCE: 13
attggagagt ttgatcctgg ctcaggacga acgctggcgg cgtgcctaat acatgcaagt 60
cgagcgaatc tgagggagct tgctcccaaa gattagcggc ggacgggtga gtaacacgtg 120
ggcaacctgc ctgtaagact gggataactc cgggaaaccg gggctaatac cggataatat 180
ctatttatac atataattag attgaaagat ggttctgcta tcacttacag atgggcccgc 240
ggcgcattag ctagttggtg aggtaacggc tcaccaaggc gacgatgcgt agccgacctg 300
agagggtgat cggccacact gggactgaga cacggcccag actcctacgg gaggcagcag 360
tagggaatct tccgcaatgg acgaaagtct gacggagcaa cgccgcgtga gtgatgaagg 420
ttttcggatc gtaaaactct gttgttaggg aagaacaagt atcggagtaa ctgccggtac 480
cttgacggta cctaaccaga aagccacggc taactacgtg ccagcagccg cggtaatacg 540
taggtggcaa gcgttgtccg gaattattgg gcgtaaagcg cgcgcaggcg gttccttaag 600
tctgatgtga aagcccacgg ctcaaccgtg gagggtcatt ggaaactggg gaacttgagt 660
gcagaagagg aaagtggaat tccaagtgta gcggtgaaat gcgtagagat ttggaggaac 720
accagtggcg aaggcgactt tctggtctgt aactgacgct gaggcgcgaa agcgtgggga 780
gcaaacagga ttagataccc tggtagtcca cgccgtaaac gatgagtgct aagtgttaga 840
gggtttccgc cctttagtgc tgcagcaaac gcattaagca ctccgcctgg ggagtacgac 900
cgcaaggttg aaactcaaag gaattgacgg gggcccgcac aagcggtgga gcatgtggtt 960
taattcgaag caacgcgaag aaccttacca ggtcttgaca tcctctgaca atcctagaga 1020
taggactttc cccttcgggg gacagagtga caggtggtgc atggttgtcg tcagctcgtg 1080
tcgtgagatg ttgggttaag tcccgcaacg agcgcaaccc ttgatcttag ttgccagcat 1140
ttagttgggc actctaaggt gactgccggt gacaaaccgg aggaaggtgg ggatgacgtc 1200
aaatcatcat gccccttatg acctgggcta cacacgtgct acaatggatg gtacaaaggg 1260
ctgcaagacc gcgaggttta gccaatccca taaaaccatt ctcagttcgg attgtaggct 1320
gcaactcgcc tacatgaagc cggaatcgct agtaatcgcg gatcagcatg ccgcggtgaa 1380
tacgttcccg ggccttgtac acaccgcccg tcacaccacg agagtttgta acacccgaag 1440
tcggtggggt aaccttttgg agccagccgc ctaaggtggg acagatgatt ggggtgaagt 1500
cgtaacaagg tagccgtatc ggaaggtgcg gctggatcac ctccttt 1547

<210> SEQ ID NO 14
<211> LENGTH: 1533
<212> TYPE: DNA
<213> ORGANISM: Pseudomonas putida

<400> SEQUENCE: 14
ctgaagagtt tgatcatggc tcagattgaa cgctggcggc aggcctaaca catgcaagtc 60
gagcggatga gaagagcttg ctcttcgatt cagcggcgga cgggtgagta atgcctagga 120

```
atctgcctgg tagtgggggga caacgtttcg aaaggaacgc taataccgca tacgtcctac    180
gggagaaagc aggggacctt cgggccttgc gctatcagat gagcctaggt cggattagct    240
agttggtgag gtaatggctc accaaggcga cgatccgtaa ctggtctgag aggatgatca    300
gtcacactgg aactgagaca cggtccagac tcctacggga ggcagcagtg gggaatattg    360
gacaatgggc gaaagcctga tccagccatg ccgcgtgtgt gaagaaggtc ttcggattgt    420
aaagcacttt aagttgggag gaagggcatt aacctaatac gttagtgttt tgacgttacc    480
gacagaataa gcaccggcta actctgtgcc agcagccgcg gtaatacaga gggtgcaagc    540
gttaatcgga attactgggc gtaaagcgcg cgtaggtggt ttgttaagtt ggatgtgaaa    600
gccccgggct caacctggga actgcatcca aaactggcaa gctagagtac ggtagagggt    660
ggtggaattt cctgtgtagc ggtgaaatgc gtagatatag gaaggaacac cagtggcgaa    720
ggcgaccacc tggactgata ctgacactga ggtgcgaaag cgtggggagc aaacaggatt    780
agataccctg gtagtccacg ccgtaaacga tgtcaactag ccgttggaat ccttgagatt    840
ttagtggcgc agctaacgca ttaagttgac cgcctgggga gtacggccgc aaggttaaaa    900
ctcaaatgaa ttgacggggg cccgcacaag cggtggagca tgtggtttaa ttcgaagcaa    960
cgcgaagaac cttaccaggc cttgacatgc agagaacttt ccagagatgg attggtgcct   1020
tcgggaactc tgacacaggt gctgcatggc tgtcgtcagc tcgtgtcgtg agatgttggg   1080
ttaagtcccg taacgagcgc aacccttgtc cttagttacc agcacgtaat ggtgggcact   1140
ctaaggagac tgccggtgac aaaccggagg aaggtgggga tgacgtcaag tcatcatggc   1200
ccttacggcc tgggctacac acgtgctaca atggtcggta cagagggttg ccaagccgcg   1260
aggtggagct aatctcacaa aaccgatcgt agtccggatc gcagtctgca actcgactgc   1320
gtgaagtcgg aatcgctagt aatcgcgaat cagaatgtcg cggtgaatac gttcccgggc   1380
cttgtacaca ccgcccgtca caccatggga gtgggttgca ccagaagtag ctagtctaac   1440
cttcgggagg acggttacca cggtgtgatt catgactggg gtgaagtcgt aacaaggtag   1500
ccgtagggga acctgcggct ggatcacctc ctt                                1533


<210> SEQ ID NO 15
<211> LENGTH: 1533
<212> TYPE: DNA
<213> ORGANISM: Pseudomonas sp.

<400> SEQUENCE: 15

ctgaagagtt tgatcatggc tcagattgaa cgctggcggc aggcctaaca catgcaagtc     60
gagcggatga cgggagcttg ctccttgatt cagcggcgga cgggtgagta atgcctagga    120
atctgcctgg tagtgggggga caacgtttcg aaaggaacgc taataccgca tacgtcctac    180
gggagaaagc aggggacctt cgggccttgc gctatcagat gagcctaggt cggattagct    240
agtaggtgag gtaatggctc acctaggcga cgatccgtaa ctggtctgag aggatgatca    300
gtcacactgg aactgagaca cggtccagac tcctacggga ggcagcagtg gggaatattg    360
gacaatgggc gaaagcctga tccagccatg ccgcgtgtgt gaagaaggtc ttcggattgt    420
aaagcacttt aagttgggag gaagggcagt aagctaatac cttgctgttt tgacgttacc    480
gacagaataa gcaccggcta actctgtgcc agcagccgcg gtaatacaga gggtgcaagc    540
gttaatcgga attactgggc gtaaagcgcg cgtaggtggt tcgttaagtt ggatgtgaaa    600
gccccgggct caacctggga actgcatcca aaactggcga gctagagtat ggtagagggt    660
ggtggaattt cctgtgtagc ggtgaaatgc gtagatatag gaaggaacac cagtggcgaa    720
```

-continued ggcgaccacc tggactgata ctgacactga ggtgcgaaag cgtggggagc aaacaggatt 780
agataccctg gtagtccacg ccgtaaacga tgtcaactag ccgttggaat ccttgagatt 840
ttagtggcgc agctaacgca ttaagttgac cgcctgggga gtacggccgc aaggttaaaa 900
ctcaaatgaa ttgacggggg cccgcacaag cggtggagca tgtggtttaa ttcgaagcaa 960
cgcgaagaac cttaccaggc cttgacatgc agagaacttt ccagagatgg attggtgcct 1020
tcgggaactc tgacacaggt gctgcatggc tgtcgtcagc tcgtgtcgtg agatgttggg 1080
ttaagtcccg taacgagcgc aacccttgtc cttagttacc agcacgttat ggtgggcact 1140
ctaaggagac tgccggtgac aaaccggagg aaggtgggga tgacgtcaag tcatcatggc 1200
ccttacggcc tgggctacac acgtgctaca atggtcggta cagagggttg ccaagccgcg 1260
aggtggagct aatctcacaa aaccgatcgt agtccggatc gcagtctgca actcgactgc 1320
gtgaagtcgg aatcgctagt aatcgcaaat cagaatgttg cggtgaatac gttcccgggc 1380
cttgtacaca ccgcccgtca caccatggga gtgggttgca ccagaagtag ctagtctaac 1440
cttcgggggg acggttacca cggtgtgatt catgactggg gtgaagtcgt aacaaggtag 1500
ccgtagggga acctgcggct ggatcacctc ctt 1533

<210> SEQ ID NO 16
<211> LENGTH: 1523
<212> TYPE: DNA
<213> ORGANISM: Streptomyces griseus

<400> SEQUENCE: 16
acggagagtt tgatcctggc tcaggacgaa cgctggcggc gtgcttaaca catgcaagtc 60
gaacgatgaa gcctttcggg gtggattagt ggcgaacggg tgagtaacac gtgggcaatc 120
tgcccttcac tctgggacaa gccctggaaa cggggtctaa taccggataa cactctgtcc 180
cgcatgggac ggggttaaaa gctccggcgg tgaaggatga gcccgcggcc tatcagcttg 240
ttggtggggt aatggcctac caaggcgacg acgggtagcc ggcctgagag ggcgaccggc 300
cacactggga ctgagacacg gcccagactc ctacgggagg cagcagtggg gaatattgca 360
caatgggcga aagcctgatg cagcgacgcc gcgtgaggga tgacggcctt cgggttgtaa 420
acctctttca gcagggaaga agcgagagtg acggtacctg cagaagaagc gccggctaac 480
tacgtgccag cagccgcggt aatacgtagg gcgcaagcgt tgtccggaat tattgggcgt 540
aaagagctcg taggcggctt gtcacgtcgg atgtgaaagc ccggggctta accccgggtc 600
tgcattcgat acgggctagc tagagtgtgg taggggagat cggaattcct ggtgtagcgg 660
tgaaatgcgc agatatcagg aggaacaccg gtggcgaagg cggatctctg ggccattact 720
gacgctgagg agcgaaagcg tggggagcga acaggattag ataccctggt agtccacgcc 780
gtaaacgttg ggaactaggt gttggcgaca ttccacgtcg tcggtgccgc agctaacgca 840
ttaagttccc cgcctgggga gtacggccgc aaggctaaaa ctcaaaggaa ttgacggggg 900
cccgcacaag cagcggagca tgtggcttaa ttcgacgcaa cgcgaagaac cttaccaagg 960
cttgacatat accggaaagc atcagagatg gtgcccccct tgtggtcggt atacaggtgg 1020
tgcatggctg tcgtcagctc gtgtcgtgag atgttgggtt aagtcccgca acgagcgcaa 1080
cccttgttct gtgttgccag catgcccttc ggggtgatgg ggactcacag gagactgccg 1140
gggtcaactc ggaggaaggt ggggacgacg tcaagtcatc atgcccctta tgtcttgggc 1200
tgcacacgtg ctacaatggc cggtacaatg agctgcgatg ccgcgaggcg gagcgaatct 1260
caaaaagccg gtctcagttc ggattggggt ctgcaactcg accccatgaa gtcggagttg 1320

-continued ctagtaatcg cagatcagca ttgctgcggt gaatacgttc ccgggccttg tacacaccgc 1380
ccgtcacgtc acgaaagtcg gtaacacccg aagccggtgg cccaacccct tgtgggaggg 1440
agctgtcgaa ggtgggactg gcgattggga cgaagtcgta acaaggtagc cgtaccggaa 1500
ggtgcggctg gatcacctcc ttt 1523

<210> SEQ ID NO 17
<211> LENGTH: 1553
<212> TYPE: DNA
<213> ORGANISM: Paenibacillus chibensis

<400> SEQUENCE: 17
cttggagagt ttgatcctgg ctcaggacga acgctggcgg cgtgcctaat acatgcaagt 60
cgagcggagt tgatgaggtg cttgcacctc tgatgcttag cggcggacgg gtgagtaaca 120
cgtaggtaac ctgcctgtaa gactgggata actaccggaa acggtagcta ataccggata 180
atttattttc tctcctgggg agataatgaa agacggagca atctgtcact tacagatggg 240
cctgcggcgc attagctagt tggtgaggta acggctcacc aaggcgacga tgcgtagccg 300
acctgagagg gtgaacggcc acactgggac tgagacacgg cccagactcc tacgggaggc 360
agcagtaggg aatcttccgc aatggacgaa agtctgacgg agcaacgccg cgtgagtgat 420
gaaggttttc ggatcgtaaa gctctgttgc cagggaagaa cgtccggtag agtaactgct 480
accggagtga cggtacctga gaagaaagcc ccggctaact acgtgccagc agccgcggta 540
atacgtaggg ggcaagcgtt gtccggaatt attgggcgta aagcgcgcgc aggcggtcac 600
ttaagtctgg tgtttaaggc caaggctcaa ccttggttcg cactggaaac tgggtgactt 660
gagtgcagaa gaggagagtg gaattccacg tgtagcggtg aaatgcgtag atatgtggag 720
gaacaccagt ggcgaaggcg actctctggg ctgtaactga cgctgaggcg cgaaagcgtg 780
gggagcaaac aggattagat accctggtag tccacgccgt aaacgatgaa tgctaggtgt 840
taggggtttc gataccettg gtgccgaagt taacacatta agcattccgc ctggggagta 900
cggtcgcaag actgaaactc aaaggaattg acggggaccc gcacaagcag tggagtatgt 960
ggtttaattc gaagcaacgc gaagaacctt accaagtctt gacatccctc tgaatcctct 1020
agagatagag gcggccttcg ggacagaggt gacaggtggt gcatggttgt cgtcagctcg 1080
tgtcgtgaga tgttgggtta agtcccgcaa cgagcgcaac ccttgatttt agttgccagc 1140
atttcggatg ggcactctag aatgactgcc ggtgacaaac cggaggaagg cggggatgac 1200
gtcaaatcat catgcccctt atgacttggg ctacacacgt actacaatgg ccagtacaac 1260
gggaagcgaa atcgcgagat ggagccaatc ctatcaaagc tggtctcagt tcggattgca 1320
ggctgcaacc cgcctgcatg aagtcggaat tgctagtaat cgcggatcag catgccgcgg 1380
tgaatacgtt cccgggtctt gtacacaccg cccgtcacac cacgagagtt tacaacaccc 1440
gaagtcggtg gggtaacccg caagggagcc agccgccgaa ggtggggtag atgattgggg 1500
tgaagtcgta acaaggtagc cgtatcggaa ggtgcggctg gatcacctcc ttt 1553

<210> SEQ ID NO 18
<211> LENGTH: 1550
<212> TYPE: DNA
<213> ORGANISM: Bacillus flexus

<400> SEQUENCE: 18
tcggagagtt tgatcctggc tcaggatgaa cgctggcggc gtgcctaata catgcaagtc 60
gagcgaactg attagaagct tgcttctatg acgttagcgg cggacgggtg agtaacacgt 120
gggcaacctg cctgtaagac tgggataact ccgggaaacc ggagctaata ccggataaca 180
ttttctcttg cataagagaa aattgaaaga tggtttcggc tatcacttac agatgggccc 240
gcggtgcatt agctagttgg tgaggtaacg gctcaccaag gcaacgatgc atagccgacc 300
tgagagggtg atcggccaca ctgggactga gacacggccc agactcctac gggaggcagc 360
agtagggaat cttccgcaat ggacgaaagt ctgacggagc aacgccgcgt gagtgatgaa 420
ggctttcggg tcgtaaaact ctgttgttag ggaagaacaa gtacaagagt aactgcttgt 480
accttgacgg tacctaacca gaaagccacg gctaactacg tgccagcagc cgcggtaata 540
cgtaggtggc aagcgttatc cggaattatt gggcgtaaag cgcgcgcagg cggtttctta 600
agtctgatgt gaaagcccac ggctcaaccg tggagggtca ttggaaactg ggaacttga 660 gtgcagaaga gaaaagcgga attccacgtg tagcggtgaa atgcgtagag atgtggagga 720
acaccagtgg cgaaggcggc tttttggtct gtaactgacg ctgaggcgcg aaagcgtggg 780
gagcaaacag gattagatac cctggtagtc cacgccgtaa acgatgagtg ctaagtgtta 840
gagggtttcc gccctttagt gctgcagcta acgcattaag cactccgcct ggggagtacg 900
gtcgcaagac tgaaactcaa aggaattgac gggggcccgc acaagcggtg gagcatgtgg 960
tttaattcga agcaacgcga agaaccttac caggtcttga catcctctga caactctaga 1020
gatagagcgt tccccttcgg gggacagagt gacaggtggt gcatggttgt cgtcagctcg 1080
tgtcgtgaga tgttgggtta agtcccgcaa cgagcgcaac ccttgatctt agttgccagc 1140
atttagttgg gcactctaag gtgactgccg gtgacaaacc ggaggaaggt ggggatgacg 1200
tcaaatcatc atgcccctta tgacctgggc tacacacgtg ctacaatgga tggtacaaag 1260
ggctgcaaga ccgcgaggtc aagccaatcc cataaaacca ttctcagttc ggattgtagg 1320
ctgcaactcg cctacatgaa gctggaatcg ctagtaatcg cggatcagca tgccgcggtg 1380
aatacgttcc cgggccttgt acacaccgcc cgtcacacca cgagagtttg taacacccga 1440
agtcggtggg gtaaccttta tggagccagc cgcctaaggt gggacagatg attggggtga 1500
agtcgtaaca aggtagccgt atcggaaggt gcggctggat cacctccttt 1550

<210> SEQ ID NO 19
<211> LENGTH: 1505
<212> TYPE: DNA
<213> ORGANISM: Clostridium pasteurianum

<400> SEQUENCE: 19
aattgagagt ttgatcctgg ctcaggacga acgctggcgg cgtgcttaac acatgcaagt 60
cgagcgagaa accttcgggt ttctagcggc ggacgggtga gtaacacgtg ggtaacctgc 120
ctcaaagagg ggaatagcct cccgaaaggg agattaatac cgcataatat tacagcttcg 180
catgaagcag taattaaagg agtaatccgc tttgagatgg acccgcggcg cattagctag 240
ttggagaggt aacggctcac caaggcgacg atgcgtagcc gacctgagag ggtgatcggc 300
cacattggaa ctgagacacg gtccagactc ctacgggagg cagcagtggg gaatattgca 360
caatgggcga aagcctgatg cagcaacgcc gcgtgagtga tgacggtctt cggattgtaa 420
agctctgtct tttgggacga taatgacggt accaaaggag gaagccacgg ctaactacgt 480
gccagcagcc gcggtaatac gtaggtggca agcgttgtcc ggatttactg ggcgtaaagg 540
atgtgtaggc ggatacttaa gtgagatgtg aaagccccgg gcttaacttg gggactgcat 600
ttcaaactgg gtgtctagag tgcaggagag gaaagcggaa ttcctagtgt agcggtgaaa 660
tgcgtagaga ttaggaagaa catcagtggc gaaggcggct ttctggactg taactgacgc 720

-continued tgaggcatga aagcgtgggg agcaaacagg attagatacc ctggtagtcc acgccgtaaa 780
cgatgagtac taggtgtagg aggtatcgac tccttctgtg ccgcagtaaa cacaataagt 840
actccgcctg ggaagtacgg tcgcaagatt aaaactcaaa ggaattgacg ggggcccgca 900
caagcagcgg agcatgtggt ttaattcgaa gcaacgcgaa gaaccttacc tagacttgac 960
atctcctgaa tagcgtagag atacgtgaag cccttcgggg caggaagaca ggtggtgcat 1020
ggttgtcgtc agctcgtgtc gtgagatgtt gggttaagtc ccgcaacgag cgcaaccctt 1080
atcattagtt gctaccatta agttgagcac tctagtgaga ctgcccgggt taaccgggag 1140
gaaggcgggg atgacgtcaa atcatcatgc cccttatgtc tagggctaca cacgtgctac 1200
aatggtgaga acaacgagat gcaataccgc gaggtggagc caaacttgaa aactcatccc 1260
agttcggatt gtaggctgaa attcgcctac atgaagttgg agttgctagt aatcgcgaat 1320
cagaatgtcg cggtgaatac gttcccgggc cttgtacaca ccgcccgtca caccatgaga 1380
gctggtaaca cccgaagtcc gtgaggtaac ctttatggag ccagcggccg aaggtgggat 1440
tagtgattgg ggtgaagtcg taacaaggta gccgtaggag aacctgcggc tggatcacct 1500
ccttt 1505

<210> SEQ ID NO 20
<211> LENGTH: 1532
<212> TYPE: DNA
<213> ORGANISM: Azotobacter vinelandii

<400> SEQUENCE: 20
ctgaagagtt tgatcatggc tcagattgaa cgctggcggc aggcctaaca catgcaagtc 60
gagcggcagc gggaccttcg ggttgccggc gagcggcgga cgggtgagta atgcctagga 120
atctgcctgt tagtggggga taacgcgggg aaactcgcgc taataccgca tacgtcctac 180
gggagaaagt gggggacctt cgggcctcac gctaacagat gagcctaggt cggattagct 240
ggttggtggg gtaacggccc accaaggcga cgatccgtaa ctggtctgag aggatgatca 300
gtcacactgg aactgagaca cggtccagac tcctacggga ggcagcagtg gggaatattg 360
gacaatgggc gaaagcctga tccagccatg ccgcgtgtgt gaagaaggtc ttcggattgt 420
aaagcacttt aagtcgggag gaagggctgt aggcgaatac cctgcagttt tgacgttacc 480
gacagaataa gcaccggcta acttcgtgcc agcagccgcg gtaatacgaa gggtgcaagc 540
gttaatcgga attactgggc gtaaagcgcg cgtaggtggt ttggtaagtt ggatgtgaaa 600
gccccgggct caacctggga actgcatcca aaactgccag gctagagtac ggtagagggt 660
ggtggaattt cctgtgtagc ggtgaaatgc gtagatatag gaaggaacac cagtggcgaa 720
ggcgaccacc tggactgata ctgacactga ggtgcgaaag cgtggggagc aaacaggatt 780
agataccctg gtagtccacg ccgtaaacga tgtcgactag ccgttgggct ccttgagagc 840
ttagtggcgc agctaacgca ttaagtcgac cgcctgggga gtacggccgc aaggttaaaa 900
ctcaaatgaa ttgacggggg cccgcacaag cggtggagca tgtggtttaa ttcgaagcaa 960
cgcgaagaac cttacctggc cttgacatcc tgcgaactgg gtagagatac ccgggtgcct 1020
tcgggaacgc agagacaggt gctgcatggc tgtcgtcagc tcgtgtcgtg agatgttggg 1080
ttaagtcccg taacgagcgc aacccttgtc cttagttacc agcacctcgg gtgggcactc 1140
taaggagact gccggtgaca aaccggagga aggtggggat gacgtcaagt catcatggcc 1200
cttacggcca gggctacaca cgtgctacaa tggtcggtac agagggttgc caagccgcga 1260
ggcggagcta atcccagaaa accgatcgta gtccggatcg cagtctgcaa ctcgactgcg 1320

```
tgaagtcgga atcgctagta atcgcgaatc agaatgtcgc ggtgaatacg ttcccgggcc   1380

ttgtacacac cgcccgtcac accatgggag tgggttgctc cagaagtagc tagtctaacc   1440

ctcgggagga cggttaccac ggagtgattc atgactgggg tgaagtcgta acaaggtagc   1500

cgtaggggaa cctgcggctg gatcacctcc tt                                 1532
```

<210> SEQ ID NO 21
<211> LENGTH: 1566
<212> TYPE: DNA
<213> ORGANISM: Virgibacillus halophilus

<400> SEQUENCE: 21

```
ttttggagag tttgatcttg gctcaggacg aacgctggcg gcgtgcctaa tacatgcaag     60

tcgagcgcgg gaagcaggat gatcctcatc tgaggtgatt cctgtggaac gagcggcgga    120

cgggtgagta acacgtgggc aacctgcctg taagatcggg ataactcgtg gaaacgcgag    180

ctaataccgg atgatacttt tcatcgcatg gtgagaagtt gaaagatggc tttaagctat    240

cacttacaga tgggcccgcg gcgcattagc tagttggtgg ggtaacggcc taccaaggca    300

acgatgcgta gccgacctga gagggtgatc ggccacactg ggactgagac acggcccaga    360

ctcctacggg aggcagcagt agggaatctt ccgcaatgga cgaaagtctg acggagcaac    420

gccgcgtgag tgatgaaggt tttcggatcg taaaactctg ttgtcaggga agaacaagtg    480

ccgtttgaat aaggcggcac cttgacggta cctgaccaga aagccccggc taactacgtg    540

ccagcagccg cggtaatacg tagggggcaa gcgttgtccg gaattattgg gcgtaaagcg    600

cgcgcaggcg gtcttttaag tctgatgtga aagcccacgg cttaaccgtg gagggtcatt    660

ggaaactgga ggacttgagt gcagaagagg agagtggaat tccatgtgta gcggtgaaat    720

gcgtagagat atggaggaac accagtggcg aaggcgactc tctggtctgc aactgacgct    780

gaggcgcgaa agcgtgggta gcgaacagga ttagataccc tggtagtcca cgccgtaaac    840

gatgagtgct aggtgttagg gggtttccgc cccttagtgc tgaagttaac gcattaagca    900

ctccgcctgg ggagtacggc cgcaaggctg aaactcaaaa gaattgacgg gggcccgcac    960

aagcggtgga gcatgtggtt taattcgaag caacgcgaag aaccttacca ggtcttgaca   1020

tcctctgaca gccttagaga taaggtgttc ccttcgggga cagagtgaca ggtggtgcat   1080

ggttgtcgtc agctcgtgtc gtgagatgtt gggttaagtc ccgcaacgag cgcaaccctt   1140

gagattagtt gccagcatta agttgggcac tctaatctga ctgccggtga caaaccggag   1200

gaaggtgggg atgacgtcaa atcatcatgc cccttatgac ctgggctaca cacgtgctac   1260

aatggatggt acagagggaa gcgaagccgc gaggtgaagc aaatcccaca aaaccattct   1320

cagttcggat tgcaggctgc aactcgcctg catgaagccg gaatcgctag taatcgcgga   1380

tcagcatgcc gcggtgaata cgttcccggg ccttgtacac accgcccgtc acaccacgag   1440

agttggtaac acccgaagtc ggtgaggtaa cctttttgga gccagccgcc gaaggtggga   1500

cgaatgattg ggtgaagtcg gtaacaaggt agccgtatcg gaaggtgcgg ctggatcacc   1560

tccttt                                                              1566
```

<210> SEQ ID NO 22
<211> LENGTH: 1561
<212> TYPE: DNA
<213> ORGANISM: Lactobacillus delbrueckii -continued

<400> SEQUENCE: 22

```
attgagagtt tgatcctggc tcaggacgaa cgctggcggc gtgcctaata catgcaagtc     60
gagcgagctg aattcaaaga tcccttcggg gtgatttgtt ggacgctagc ggcggatggg    120
tgagtaacac gtgggcaatc tgccctaaag actgggatac cacttggaaa caggtgctaa    180
taccggataa caacatgaat cgcatgattc aagtttgaaa ggcggcgcaa gctgtcactt    240
taggatgagc ccgcggcgca ttagctagtt ggtggggtaa aggcctacca aggcaatgat    300
gcgtagccga gttgagagac tgatcggcca cattgggact gagacacggc ccaaactcct    360
acgggaggca gcagtaggga atcttccaca atggacgcaa gtctgatgga gcaacgccgc    420
gtgagtgaag aaggtcttcg gatcgtaaag ctctgttgtt ggtgaagaag gatagaggca    480
gtaactggtc tttatttgac ggtaatcaac cagaaagtca cggctaacta cgtgccagca    540
gccgcggtaa tacgtaggtg gcaagcgttg tccggattta ttgggcgtaa agcgagcgca    600
ggcggaatga taagtctgat gtgaaagccc acggcttaac cgtggaactg catcggaaac    660
tgtcattctt gagtgcagaa gaggagagtg gaactccatg tgtagcggtg gaatgcgtag    720
atatatggaa gaacaccagt ggcgaaggcg gctctctggt ctgcaactga cgctgaggct    780
cgaaagcatg ggtagcgaac aggattagat accctggtag tccatgccgt aaacgatgag    840
cgctaggtgt tggggacttt ccggttctca gtgccgcagc aaacgcgtta agcgctccgc    900
ctggggagta cgaccgcaag gttgaaactc aaaggaattg acgggggccc gcacaagcgg    960
tggagcatgt ggtttaattc gaagcaacgc gaagaacctt accaggtctt gacatcctgc   1020
gctacaccta gagataggtg gttcccttcg gggacgcaga gacaggtggt gcatggctgt   1080
cgtcagctcg tgtcgtgaga tgttgggtta agtcccgcaa cgagcgcaac ccttgtcttt   1140
agttgccatc attaagttgg gcactctaaa gagactgccg gtgacaaacc ggaggaaggt   1200
ggggatgacg tcaagtcatc atgcccctta tgacctgggc tacacacgtg ctacaatggg   1260
cagtacaacg agaagcgaac ccgcgagggt aagcggatct cttaaagctg ctctcagttc   1320
ggactgcagg ctgcaactcg cctgcacgaa gctggaatcg ctagtaatcg cggatcagca   1380
cgccgcggtg aatacgttcc cgggccttgt acacaccgcc cgtcacacca tggaagtctg   1440
caatgcccaa agtcggtgag ataaccttta taggagtcag ccgcctaagg cagggcagat   1500
gactggggtg aagtcgtaac aaggtagccg taggagaacc tgcggctgga tcacctcctt   1560
t                                                                   1561
```

MICROBIAL COATING OF CONTROLLED-RELEASE FERTILIZERS

CROSS REFERENCE TO RELATED APPLICATION

This application claims priority to U.S. Provisional Application No. 62/803,062 filed Feb. 8, 2019, which is incorporated herein by reference in its entirety.

FIELD

This disclosure relates to fertilizer compositions including one or more microbial species and a polymer coating and methods of making and using the compositions.

BACKGROUND

The use of dry, chemical fertilizers or plant growth promoting chemicals is common practice in agriculture worldwide. Controlled-release dry chemical fertilizers contain one or more plant nutrients in a form that makes it/them unavailable for immediate plant uptake after the fertilizer is applied. However, the bioavailability of these dry-formulated fertilizers (such as ammonium nitrate, urea, ammonium phosphate, or potassium chloride) is significantly increased over their quick release counterparts. Controlled-release fertilizers (CRF) are typically coated or encapsulated with inorganic or organic materials that control the rate, pattern, and duration of plant nutrient release into the rhizosphere as the crop is prepared to take up and utilize these nutrients. The coating serves to protect the applied nutrient, such as nitrogen in the form of urea, from becoming unavailable to the crop due to leaching, denitrification or other soil-related factors. In addition, the release rate of a CRF fertilizer is designed to meet crop nutrient requirements over time.

The use of microbe-based plant growth promoting formulations is also common practice. Microbe-based plant biostimulants offer sustainable agriculture practices that protect the health of the ecosystem. Moreover, supplementation of the plant and soil microbiome with beneficial microorganisms (such as Rhizobacteria) has potential in promoting plant growth and plant fitness, increasing productivity (Kloepper and Schroth, *Proceedings of the 4th International Conference on Plant Pathogenic Bacteria*, Vol. II, pp. 879-882, 1978; Lugtenberg and Kamilova, *Ann. Rev. Microbiol.* 63:541-556, 2009; Vessey, *Plant Soil* 255: 571-586, 2003), improving soil fertility and reducing chemical inputs (Adesmoye et al., *Microb. Ecol.* 58:921-929, 2009), resulting in more sustainable agricultural practices.

SUMMARY

The co-application of chemical and microbial fertilizers has demonstrated to have positive effects on many crops (Latha et al., *Int. J. Pure App. Biosci.* 2:119-124, 2014; Erkovan et al., *Turkish J. Field Crops* 15:12-17, 2010; Adesmoye et al., *Microb. Ecol.* 58:921-929, 2009; Sharma and Banik, J. Plant Nutrition 37:209-223, 2014; Shaheen et al., *Australian J. Basic Appl. Sci.* 1:307-312, 2007). Disclosed herein are novel multi-component fertilizer and/or plant biostimulant compositions that include one or more microbes and one or more fertilizers/macronutrients (such as controlled-release fertilizers/macronutrient) as dry formulations.

Disclosed herein are compositions including a core particle including at least one fertilizer nutrient and a shell substantially covering the core particle, wherein the shell includes at least one polymer layer or wax layer and one or more species of microbes (such as a population of cells from at least one species of microbes). In some embodiments, at least one of the polymer layer and/or the wax layer includes the one or more species of microbes. In some examples, the composition includes two or more (such as 2, 3, 4, or more) polymer layers and/or wax layers substantially covering the fertilizer particle and at least one of the polymer layers and/or at least one of the wax layers includes the one or more species of microbes. In some examples, one or more polymer layers may alternate with one or more layers of wax. In some examples, at least the outer layer (such as an outer polymer layer or an outer wax layer) includes the microbes. In still further examples, the one or more species of microbes are included between layers, for example, between two polymer layers, between two wax layers, or between a polymer layer and a wax layer.

In some embodiments, the compositions include cells of one or more (such as 1, 2, 3, 4, 5, 6, 7, 8, 9, 10, 11, 12, 13, 14, 15, 16, 17, 18, 19, 20, 21, 22, or more) species of microbes. In one example, the one or more species of microbes are selected from *Lactobacillus delbrueckii, Virgibacillus halophilus, Azotobacter vinelandii, Clostridium pasteurianum, Paenibacillus chibensis, Streptomyces griseus, Pseudomonas sp* (closely related to *P. entomophila, P. fluorescens*, and *P. putida*; for example, a microbial species with 16S rRNA sequence with at least 99% sequence identity to SEQ ID NO: 17), *Pseudomonas putida, Bacillus sp* (closely related to *B. kochii, B. pocheonensis*, and *Bacillus sp* (strain R-27341; for example, a microbial species with a 16S rRNA sequence with at least 99% sequence identity to SEQ ID NO: 15), *Bacillus amyloliquefaciens, Oceanobacillus oncorhynchi, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*. In another example, the one or more species of microbes include *Bacillus amyloliquefaciens, Bacillus flexus, Bacillus licheniformis, Bacillus megaterium, Bacillus subtilis, Lactobacillus delbrueckii, Paenibacillus chibensis, Paenibacillus cookii*, or a combination of two or more thereof. In an additional example, the one or more species of microbes include *Bacillus amyloliquefaciens, Bacillus flexus, Bacillus licheniformis, Bacillus megaterium, Bacillus subtilis, Lactobacillus delbrueckii*, or a combination of two or more thereof.

Also disclosed are methods of making the composition. In some embodiments, the methods include contacting a fertilizer granule with a mixture comprising a polymer, pre-polymer, and/or oligomer and one or more species of microbes (such as a population of cells including one or more species of microbes) and polymerizing the polymer to form a layer substantially covering the fertilizer granule and/or contacting a fertilizer granule with a mixture including wax and one or more species of microbes (such as a population of cells including one or more species of microbes) to form a layer substantially covering the fertilizer granule. In some examples, the method includes mixing the microbes in a liquid form with the polymer, pre-polymer, and/or oligomer or wax to form the mixture prior to contacting the mixture with the fertilizer granule. In other examples, the method includes mixing the microbes in a freeze-dried form with the polymer, pre-polymer, and/or oligomer or wax to form the mixture prior to contacting the mixture with the fertilizer granule.

Also disclosed herein are methods of using the disclosed compositions that include contacting soil, plants, plant parts, or seeds with the composition. The compositions may be applied to soil, plant, plant parts, and/or seeds alone or in combination with additional component(s).

The foregoing and other features of the disclosure will become more apparent from the following detailed description, which proceeds with reference to the accompanying figures.

SEQUENCES

Figure 1:
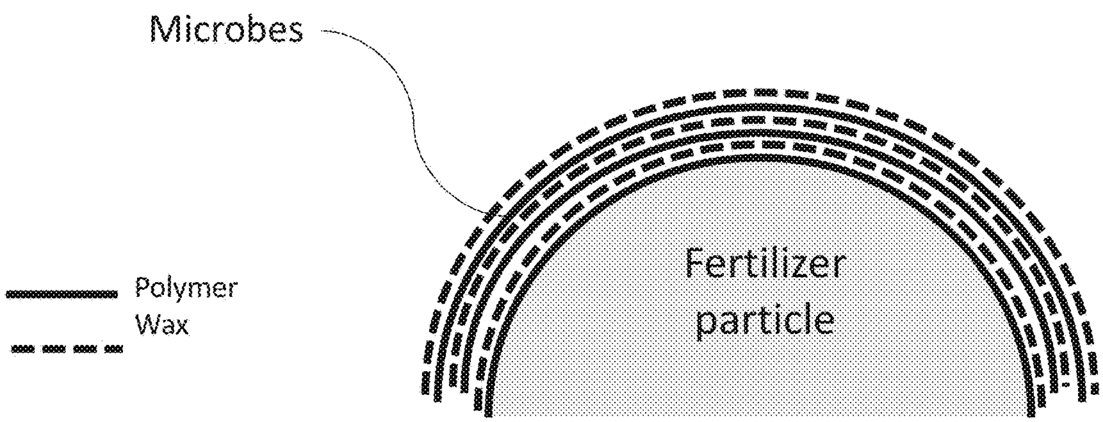
FIG. 1 is a schematic diagram of an exemplary fertilizer-microbial composition embodiment.

Any nucleic acid and amino acid sequences listed herein or in the accompanying sequence appendix are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Feb. 7, 2020, and is about 48 kilobytes, which is incorporated by reference herein.

SEQ ID NO: 1 is a 16S rDNA nucleotide sequence from a microbe identified as *Bacillus megaterium.*

SEQ ID NO: 2 is a 16S rDNA nucleotide sequence from a microbe identified as *Lactobacillus casei/paracasei.*

SEQ ID NO: 3 is a 16S rDNA nucleotide sequence from a microbe identified as *Clostridium beijerinckii.*

SEQ ID NO: 4 is a 16S rDNA nucleotide sequence from a microbe identified as *Acetobacter pasteurianus.*

SEQ ID NO: 5 is a 16S rDNA nucleotide sequence from a microbe identified as *Lactobacillus buchneri.*

SEQ ID NO: 6 is a 16S rDNA nucleotide sequence from a microbe identified as *Bacillus subtilis.*

SEQ ID NO: 7 is a 16S rDNA nucleotide sequence from a microbe identified as *Paenibacillus cookii.*

SEQ ID NO: 8 is a 16S rDNA nucleotide sequence from a microbe identified as *Lactobacillus vini.*

SEQ ID NO: 9 is a 16S rDNA nucleotide sequence from a microbe identified as *Bacillus licheniformis.*

SEQ ID NO: 10 is a 16S rDNA nucleotide sequence from a microbe identified as *Paenibacillus lautus.*

SEQ ID NO: 11 is a 16S rDNA nucleotide sequence from a microbe identified as *Oceanobacillus oncorhynchi.*

SEQ ID NO: 12 is a 16S rDNA nucleotide sequence from a microbe identified as *Bacillus amyloliquefaciens.*

SEQ ID NO: 13 is a 16S rDNA nucleotide sequence from a microbe identified as *Bacillus sp.*

SEQ ID NO: 14 is a 16S rDNA nucleotide sequence from a microbe identified as *Pseudomonas putida.*

SEQ ID NO: 15 is a 16S rDNA nucleotide sequence from a microbe identified as *Pseudomonas sp.*

SEQ ID NO: 16 is a 16S rDNA nucleotide sequence from a microbe identified as *Streptomyces griseus.*

SEQ ID NO: 17 is a 16S rDNA nucleotide sequence from a microbe identified as *Paenibacillus chibensis.*

SEQ ID NO: 18 is a 16S rDNA nucleotide sequence from a microbe identified as *Bacillus flexus.*

SEQ ID NO: 19 is a 16S rDNA nucleotide sequence from a microbe identified as *Clostridium pasteurianum.*

SEQ ID NO: 20 is a 16S rDNA nucleotide sequence from a microbe identified as *Azotobacter vinelandii.*

SEQ ID NO: 21 is a 16S rDNA nucleotide sequence from a microbe identified as *Virgibacillus halophilus.*

SEQ ID NO: 22 is a 16S rDNA nucleotide sequence from a microbe identified as *Lactobacillus delbrueckii.*

DETAILED DESCRIPTION

Disclosed herein are compositions including a fertilizer particle and at least one layer (such as at least one polymer layer or wax layer) substantially covering the fertilizer particle, wherein the layer includes one or more species of microbes (such as a population of cells from at least one species of microbes), and methods of their use. Also disclosed are compositions including a fertilizer particle and at least two layers (such as at least two polymer layers, at least two wax layers, or at least one polymer layer and at least one wax layer), wherein one or more one or more species of microbes (such as a population of cells from at least one species of microbes) are included between the at least two layers, and methods of their use. Without being bound by theory, it is believed that these compositions (which are in some instances referred to as "controlled-release fertilizers") may provide benefits to plants and/or soil by 1) increasing the benefit of the microbes due to their release over time, 2) increasing the benefit of the fertilizer to the plants (e.g., increasing nitrogen uptake), and/or 3) enabling increased bioavailability of fertilizer(s) and/or micronutrient(s) to plants.

I. Terms

Unless otherwise noted, technical terms are used according to conventional usage. Definitions of common terms in molecular biology may be found in Krebs et al., *Lewin's Genes XI*, published by Jones and Bartlett Learning, 2012 (ISBN 1449659853); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 2011 (ISBN 8126531789); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Contacting: Placement in direct physical association, including both in solid and liquid form. For example, contacting can occur with one or more microbes (such as the microbes in a microbial consortium) and a biological sample in solution. Contacting can also occur with one or more microbes (such as the microbes in a microbial consortium) and soil, plants, and/or plant parts (such as foliage, stem, seedling, roots, and/or seeds).

Controlled-release: Controlled-release fertilizer includes water-soluble fertilizer that is encased within a coating (such as a polymer coating), forming a round prill. The coating has reduced permeability, solubility, and/or slower degradation to provide a slow or controlled release of the fertilizer, for example to release the fertilizer over an extended period of time. In some examples, the coating has small holes through which water passes into the prill, which solubilizes the fertilizer, and then the fertilizer slowly leaches from the prill. Controlled-release fertilizers have different N—P—K analyses and may or may not include micronutrients. They also have different length of releases, expressed as months, days or "Type," which determine how long the controlled release fertilizer will persist.

Culture medium: A synthetic set of culture conditions including nutrients to support the viability, function, and/or growth of a specific population of cells, such as one or more microbial species. Culture media generally include components such as a carbon source, a nitrogen source and a buffer to maintain pH. Additional components in culture media also may include one or more of hormones, growth factors, protease inhibitors, protein hydrolysates, shear force protectors, proteins, vitamins, trace elements, inorganic salts, minerals, and/or lipids.

Culturing: Intentional growth of one or more organisms or cells in the presence of assimilable sources of carbon, nitrogen and mineral salts. In an example, such growth can take place in a solid or semi-solid nutritive medium, or in a liquid medium in which the nutrients are dissolved or suspended. In a further example, the culturing may take place on a surface or by submerged culture. The nutritive medium can be composed of complex nutrients or can be chemically defined.

Fermenting: A process that results in the breakdown of complex organic compounds into simpler compounds, for example by microbial cells (such as bacteria and/or fungi). The fermentation process may occur under aerobic conditions, anaerobic conditions, or both (for example, in a large volume where some portions are aerobic and other portions are anaerobic). In some non-limiting embodiments, fermenting includes the enzymatic and/or non-enzymatic breakdown of compounds present in aquatic animals or animal by-products, such as chitin.

Fertilizer granule: A fertilizer that is dry and is in pellet form. Dry fertilizers are generally incorporated into granules through a process referred to as granulation, where agglomeration or crystallization is the mechanism responsible for granulate formation and growth. In some examples, such as prilling, particles are formed by cooling liquid droplets by bringing them into contact with cooling air as they are falling in a prill tower. The droplets crystallize thereby forming solid particles. In other examples, such as fluid bed granulation, solid seed particles are grown by placing them in a fluid bed and covering them with liquid droplets or films, for example, of urea melt. Cooling air is used to crystallize the urea melt onto the particles which thereby grow in size. Fertilizer blends can be created by mixing individual granular fertilizer of known analysis in the proper ratio to create the desired blend.

Isolated: An "isolated" biological component (such as a nucleic acid, protein or organism) has been substantially separated or purified away from other biological components (such as other cells, cell debris, or other proteins or nucleic acids). Biological components that have been "isolated" include those components purified by standard purification methods. The term also embraces recombinant nucleic acids, proteins or microbes, as well as chemically synthesized nucleic acids or peptides. The term "isolated" (or "enriched" or "purified") does not require absolute purity, and can include microbes or molecules that are at least 50% isolated, such as at least 75%, 80%, 90%, 95%, 98%, 99% or even 100% isolated.

Microbe: A microorganism, including but not limited to bacteria, archaebacteria, fungi, and algae (such as microalgae). In some examples, microbes are single-cellular organisms (for example, bacteria, cyanobacteria, some fungi, or some algae). In other examples, the term microbes includes multi-cellular organisms, such as certain fungi or algae (for example, multicellular filamentous fungi or multicellular algae).

Microbial composition: A composition (which can be solid, liquid, or at least partially both) that includes cells of at least one type (or species) of microbe (or a population of cells of at least one type of microbe). In some examples, a microbial composition comprises cells of one or more types (species) of microbes (or one or more populations of microbes) in a liquid medium (such as a storage, culture, or fermentation medium), for example, as a suspension in the liquid medium. In other examples, a microbial composition includes cells of one or more types (species) of microbes (or one or more populations of microbes) on the surface of or embedded in a solid or gelatinous medium (including but not limited to a culture plate), or a slurry or paste.

Microbial consortium: A mixture, association, or assemblage of cells of two or more microbial species, which in some instances are in physical contact with one another. The microbes in a consortium may affect one another by direct physical contact or through biochemical interactions, or both. For example, microbes in a consortium may exchange nutrients, metabolites, or gases with one another. Thus, in some examples, at least some of the microbes in a consortium are metabolically interdependent. Such interdependent interactions may change in character and extent through time and with changing culture conditions.

II. Fertilizer-Microbial Compositions

Disclosed herein are compositions including a fertilizer particle and at least one layer substantially covering the fertilizer particle, wherein the layer includes one or more species of microbes (such as a population of cells from at least one species of microbes). In some embodiments, the at least one layer including one or more species of microbes is a polymer layer, a wax layer, or a combination thereof. In other embodiments, the composition includes one or more layers wherein at least one layer is a polymer layer and at least one layer includes one or more species of microbes (such as a population of cells from at least one species of microbes). In some examples, the composition includes two or more (such as 2, 3, 4, or more) polymer layers substantially covering the fertilizer particle and at least one of the polymer layers includes one or more species of microbes. The polymer layers may alternate with a layer of wax. In some examples, at least the outer layer (such as an outer polymer layer or an outer wax layer) includes the microbes. In still further examples, the one or more species of microbes are included between layers, for example, between at least two polymer layers, between at least two wax layers, or between at least one polymer layer and at least one wax layer.

In some embodiments, the composition includes a fertilizer particle and at least one polymer layer substantially covering the fertilizer particle, wherein the at least one polymer layer comprises one or more species of microbes (for example, a population of cells including one or more species of microbes). In some examples, the polymer layer is about 1 to 500 μm thick, for example about 1-50 μm, about 10-100 μm, about 75-250 μm, about 150-300 μm, or about 200-500 μm thick (such as about 1 μm, about 5 μm, about 10 μm, about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, or about 500 μm). In some examples, the at least one polymer layer includes 2, 3, 4, 5, 6, 7, 8, 9, 10, 11, 12, 13, 14, 15, 16, 17, 18, 19, 20, 21, or 22 species of microbes (such as a population of cells including 2-22 species of microbes).

In some examples, the composition includes two or more (such as 2, 3, 4, 5, or more) polymer layers substantially covering the fertilizer particle. The polymer layers optionally alternate with a layer of wax. In some example, the wax layer is about 1-50 μm thick, for example about 1-5 μm, about 3-10 μm, about 10-25 μm, about 20-40 μm, or about 30-50 μm (for example, about 1 μm, about 2 μm, about 3 μm, about 4 μm, about 5 μm, about 6 μm, about 7 μm, about 8 μm, about 9 μm, about 10 μm, about 12 μm, about 15 μm, about 20 μm, about 25 μm, about 30 μm, about 35 μm, about 40 μm, about 45 μm, or about 50 μm). For example, if the composition includes two polymer layers, there is a layer of wax between the two polymer layers. In some embodiments including two or more polymer layers, at least the outermost layer of polymer includes one or more species of microbes. In other embodiments including two or more polymer layers, any (e.g., inner or outer) or all of the layers can include one or more species of microbes. In one particular non-limiting example, the composition includes (from innermost to outermost) a fertilizer particle coated with a layer of polymer substantially covering the particle, a layer of wax, a polymer layer, a layer of wax, a polymer layer including one or more species of microbes, and a layer of wax. A schematic of this exemplary composition is shown in FIG. 1.

In other examples, the composition includes at least one polymer layer and at least one wax layer substantially covering the fertilizer particle. The at least one polymer layer, the at least one wax layer, or a combination thereof includes one or more species of microbes (for example, a population of cells including one or more species of microbes). In still further examples, the one or more species of microbes is included between two layers substantially covering the fertilizer particle, such as between a polymer layer and a wax layer.

In some embodiments, the core particle includes at least one fertilizer nutrient, which in some examples is selected from an N—P—K fertilizer, such as a fertilizer particle. Fertilizer particles include granules that include one or more nitrogen, phosphorous, and/or potassium (NPK) sources, such as urea, monoammonium phosphate, diammonium phosphate, ammonium nitrate, potassium nitrate, potassium sulfate, and ammonium sulfate. Other fertilizer compounds can be selected by one of ordinary skill in the art. Fertilizer granules are generally about 0.5-5 mm in diameter, for example, about 0.5-2 mm, about 1-4 mm, about 1.5-3 mm, or about 2-5 mm (for example, about 0.5 mm, about 1 mm, about 1.5 mm, about 2 mm, about 2.5 mm, about 3 mm, about 3.5 mm, about 4 mm, about 4.5 mm, or about 5 mm). In some embodiments, the fertilizer particle is a nitrogen source, such as urea. For example, the fertilizer particle may be a urea granule.

In some embodiments, the polymer is polyurethane, urethane, a resin (for example, polyester resin), latex, or other biodegradable polymers. In some examples, the polymer is urethane, for example, formed by reaction of polyol with a diisocyanate (such as MDI or TDI). In some examples, the polymer is non-water soluble.

In some embodiments, the disclosed compositions include one or more layers of wax. Exemplary waxes include paraffin, olefin blend, and microcrystalline wax. In some examples, the wax is olefin or paraffin. In some examples, the wax has a melting point of about 100-200° F., such as about 120-180° F., about 130-160° F., or about 140-150° F.

In some embodiments, the composition includes one or more species of microbes (such as a population of cells from one or more microbial species) selected from *Lactobacillus delbrueckii, Virgibacillus halophilus, Azotobacter vinelandii, Clostridium pasteurianum, Paenibacillus chibensis, Streptomyces griseus, Pseudomonas sp* (closely related to *P. entomophila, P. fluorescens*, and *P. putida*; for example, a microbial species with 16S rRNA sequence with at least 99% sequence identity to SEQ ID NO: 17), *Pseudomonas putida, Bacillus sp* (closely related to *B. kochii, B. pocheonensis*, and *Bacillus sp* (strain R-27341; for example, a microbial species with a 16S rRNA sequence with at least 99% sequence identity to SEQ ID NO: 15), *Bacillus amyloliquefaciens, Oceanobacillus oncorhynchi, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*. In some examples, the one or more species of microbes are selected from microbes having a 16S rRNA sequence with at least 99% sequence identity (such as 99.1%, 99.2%, 99.3%, 99.4%, 99.5%, 99.6%, 99.7%, 99.8%, 99.9%, or 100% identity) to one of SEQ ID NOs: 1-22. In other examples, the one or more species of microbes include the collection of microbes deposited with the American Type Culture Collection (ATCC, Manassas, Va.) on Jul. 1, 2016 and assigned deposit number PTA-123288, PTA-123298, PTA-123289, or a combination of two or more thereof (such as 2, 3, 4, 5, 6, 7, 8, 9, 10, 11, 12, 13, 14, 15, 16, 17, 18, 19, 20, 21, or 22 thereof).

In other embodiments, the one or more species of microbes (such as a population of cells from one or more microbial species) includes or consists of *Bacillus amyloliquefaciens, Bacillus flexus, Bacillus licheniformis, Bacillus megaterium, Bacillus subtilis, Lactobacillus delbrueckii, Paenibacillus chibensis, Paenibacillus cookii*, or a combination of two or more thereof (such as 2, 3, 4, 5, 6, 7, or 8 thereof). In some examples, the one or more species of microbes have a 16S rDNA sequence having at least 99% sequence identity (such as 99.1%, 99.2%, 99.3%, 99.4%, 99.5%, 99.6%, 99.7%, 99.8%, 99.9%, or 100% identity) to one of SEQ ID NOs: 1, 6, 7, 9, 12, 17, 18, and 22.

In other embodiments, the one or more species of microbes (such as a population of cells from one or more microbial species) includes or consists of *Bacillus amyloliquefaciens, Bacillus flexus, Bacillus licheniformis, Bacillus megaterium, Bacillus subtilis*, and *Lactobacillus delbrueckii* or a combination of two or more (such as 2, 3, 4, 5, or 6) thereof. In some examples, the one or more species of microbes have a 16S rDNA sequence having at least 99% sequence identity (such as 99.1%, 99.2%, 99.3%, 99.4%, 99.5%, 99.6%, 99.7%, 99.8%, 99.9%, or 100% identity) to one of SEQ ID NOs: 1, 6, 9, 12, 18, and 22.

In additional embodiments, the one or more species of microbes(such as a population of cells from one or more microbial species) includes or consists of *Bacillus amyloliquefaciens, Bacillus flexus, Bacillus licheniformis, Bacillus megaterium, Bacillus subtilis, Bacillus sp* (strain R-27341; for example, a microbial species with a 16S rRNA sequence with at least 99% sequence identity to SEQ ID NO: 15), *Lactobacillus casei/paracasei, Lactobacillus delbrueckii, Paenibacillus chibensis, Paenibacillus cookii, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), or a combination of two or more (such as 2, 3, 4, 5, 6, 7, 8, 9, 10, or 11) thereof. In some examples, the one or more species of microbes have a 16S rDNA sequence having at least 99% sequence identity (such as 99.1%, 99.2%, 99.3%, 99.4%, 99.5%, 99.6%, 99.7%, 99.8%, 99.9%, or 100% identity) to one of SEQ ID NOs: 1, 2, 6, 7, 9, 10, 12, 13, 17, 18, and 22.

In further embodiments, the one or more species of microbes (such as a population of cells from one or more microbial species) includes or consists of *Bacillus amyloliquefaciens, Bacillus flexus, Bacillus megaterium, Bacillus subtilis, Lactobacillus delbrueckii, Paenibacillus chibensis, Paenibacillus cookii, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), or a combination of two or more (such as 2, 3, 4, 5, 6, 7, or 8) thereof. In some examples, the one or more species of microbes have a 16S rDNA sequence having at least 99% sequence identity (such as 99.1%, 99.2%, 99.3%, 99.4%, 99.5%, 99.6%, 99.7%, 99.8%, 99.9%, or 100% identity) to one of SEQ ID NOs: 1, 6, 7, 10, 12, 17, 18, and 22.

In further embodiments, the one or more species of microbes have a combination of desirable metabolic characteristics or activities, including nitrogen metabolism activity (such as denitrification, nitrogen fixation, and/or urease production), salt tolerance (for example, growth at 72 hours in medium containing 1%, 2.5%, 5%, 7.5%, or 10% salt), phosphate and/or calcium and/or zinc salt solubilization activity, cellulolytic and/or chitinolytic activity (such as GlcNAc degradation, chitin degradation, and/or cellobiose degradation), malic acid metabolism activity (such as malic acid assimilation), phytohormone (such as indole (auxin)) production activity, sulfur metabolism activity (such as sulfur oxidation, sulfur reduction, or ability to metabolize inorganic sulfate salts), iron metabolizing activity (such as iron binding activity (siderophores)), and/or dephosphorylation of organic phosphate activity. As exemplified in Example 1, a single microbial species may have more than one of the listed activities, thus, in some examples a composition including cells with a given number of the listed activities will not necessarily have cells of that number of different microbial species.

III. Methods of Making Fertilizer-Microbial Compositions

Disclosed herein are methods of preparing the fertilizer-microbial compositions. In some embodiments, the methods include contacting a fertilizer granule with a mixture comprising a polymer, pre-polymer, and/or oligomer and one or more species of microbes (such as a population of cells including one or more species of microbes) and polymerizing the polymer to form a layer of the mixture substantially covering the fertilizer granule, to form a coated fertilizer granule. In some examples, the polymer is polyurethane and the contacting and polymerization (for example, contacting with polyol and methylene diphenyl diisocyanate (MDI) and polymerizing to form polyurethane) are carried out at about 120-180° F., such as about 120-140° F., about 130-150° F., about 140-165° F., or about 130-140° F. (for example, about 120° F., about 130° F., about 140° F., about 150° F., about 160° F., or about 170° F., for about 5-10 minutes. The one or more species of microbes include those described in Section II, though other microbes can also be utilized. In some examples, the fertilizer granule is a urea particle.

In some examples, the method includes mixing the microbes in a liquid form with the polymer, pre-polymer, and/or oligomer to form the mixture of the polymer and microbes applied to the fertilizer granule (for example, applied and polymerized on the granule). In other examples, the method includes mixing the microbes in a freeze-dried form with the polymer, pre-polymer, or oligomer to from the mixture of polymer and microbes applied to the fertilizer granule (for example, applied and polymerized on the granule). The mixture may also include other components, such as one or more catalysts, polymerizing agents, microbial nutrients (such as a carbon source, e.g., at least one sugar), or other compounds. In one non-limiting example, the microbes are mixed with polyol and/or a diisocyanate (such as MDI or TDI) prior to polymerization. In some examples, the polyol and diisocyanate and applied to the particle separately and sequentially polymerized. Therefore, in some examples, the microbes are added to the polyol, the diisocyanate, or both.

In some embodiments, the method further includes contacting the coated fertilizer granule with wax to form a layer substantially covering the coated fertilizer granule to form a wax-coated fertilizer granule and contacting the wax-coated fertilizer granule with a polymer to form a layer substantially covering the wax-coated fertilizer granule; and polymerizing the polymer. Two or more layers (such as 2, 3, 4, 5, or more layers) of alternating polymer and wax can be applied to the fertilizer granule, with the outer layer being a wax layer or a polymer (for example, polyurethane or urethane layer). In some embodiments, at least the outermost layer of polymer includes the one or more species of microbes. In other examples, any (e.g., inner, outer, or intermediate (if present) layers) or all of the layers can include one or more species of microbes. In such embodiments, one or more species of microbes (in liquid or freeze-dried form) are mixed with the polymer prior to application to the fertilizer particle to form the desired layer containing the one or more species of microbes.

In other embodiments, the methods include contacting a fertilizer granule with a mixture comprising a wax and one or more species of microbes (such as a population of cells including one or more species of microbes) to form a layer of the mixture substantially covering the fertilizer granule, to form a coated fertilizer granule. In some examples, the method includes mixing the microbes in a liquid form with the wax to form the mixture of the wax and microbes applied to the fertilizer granule. In other examples, the method includes mixing the microbes in a freeze-dried form with the wax to form the mixture of polymer and microbes applied to the fertilizer granule. The mixture may also include other components, such as one or more catalysts, polymerizing agents, microbial nutrients (such as a carbon source, e.g., at least one sugar), or other compounds. In some examples, the wax is paraffin, olefin blend, or microcrystalline wax.

In still further embodiments, the methods include contacting a fertilizer granule with a polymer (such as a polymer, pre-polymer, and/or oligomer) and polymerizing the polymer to form a layer of the polymer substantially covering the fertilizer granule, contacting the fertilizer granule with wax to form a layer of wax substantially covering the fertilizer granule, and contacting the fertilizer granule with a mixture of microbes (for example, a liquid and/or freeze-dried microbes) to form a layer of microbes substantially covering the fertilizer granule. These steps may be performed in any order and repeated one or more times. Thus is some examples, the method includes coating a fertilizer granule with polymer to form a polymer-coated granule, coating the polymer-coated granule with microbes to form a microbial-coated, polymer-coated granule, and coating the microbial-coated, polymer-coated granule to form a wax-coated, microbial-coated, polymer-coated granule. In other examples, the microbial coating is applied between polymer coatings and/or the microbial coating is applied between wax coatings. An exemplary, non-limiting method of producing a fertilizer granule with microbes included between layers is provided in Example 9.

IV. Methods of Use

The disclosed fertilizer-microbial compositions can be used to treat soil, plants, or plant parts (such as roots, stems, foliage, seeds, or seedlings). In some examples, treatment with the disclosed compositions improve plant growth, improve stress tolerance, and/or increase crop yield. In some embodiments the methods include contacting soil, plants (such as plant foliage, stems, roots, seedlings, or other plant parts), or seeds with a fertilizer-microbial composition disclosed herein. The methods may also include growing the treated plants, plant parts, or seeds and/or cultivating plants, plant parts, or seeds in treated soil.

In particular embodiments, the disclosed fertilizer-microbe compositions are applied directly to the soil. Application can be by one or more of broadcast, pre-plant band, side-band or mid-row band at planting, and seed row placement. Application rates can be compatible with standard grower practices for a given crop and geography. Appropriate application rates and timing of application can be selected based on the type of fertilizer, type of application, and the crop, as well as soil and weather conditions.

In one non-limiting example, application rates of nitrogen on field corn in the form of coated urea disclosed herein is about 150 to 250 pounds of nitrogen per acre (such as about 150-175, about 175-200, about 200-225, or about 225-250 pounds of nitrogen per acre). In such examples, the composition is either applied by broadcast and left on the surface of the soil or broadcast and lightly incorporated into the soil. Application rates will vary based on the grower's target yield and take into account soil types, previous crops, as well as many other factors. For other crops (for example, wheat, rice, cotton) the rates of fertilizer application are based on target yields, residual nutrients, crop advisor recommendations, and can be selected by one of ordinary skill in the art.

In some examples, treatment of soil, seeds, plants, or plant parts with a disclosed composition increases plant growth (such as overall plant size, amount of foliage, root number, root diameter, root length, production of tillers, fruit production, pollen production, and/or seed production) by at least about 5% (for example, at least about 10%, at least about 30%, at least about 50%, at least about 75%, at least about 100%, at least about 2-fold, at least about 3-fold, at least about 5-fold, at least about 10-fold, or more). In other examples, the disclosed methods result in increased crop production by about 10-75% (such as about 20-60% or about 30-50%) compared to untreated crops. Other measures of crop performance include quality of fruit, yield, starch or solids content, sugar content or brix, shelf-life of fruit or harvestable product, production of marketable yield or target size, quality of fruit or product, grass tillering and resistance to foot traffic in turf, pollination and fruit set, bloom, flower number, flower lifespan, bloom quality, rooting and root mass, crop resistance to lodging, abiotic stress tolerance to heat, drought, cold and recovery after stress, adaptability to poor soils, level of photosynthesis and greening, and plant health. To determine efficacy of products, controls include the same agronomic practices without addition of microbes, performed in parallel.

The disclosed methods and compositions can be used in connection with any crop (for example, for direct crop treatment or for soil treatment prior to or after planting). Exemplary crops include, but are not limited to alfalfa, almond, banana, barley, broccoli, cabbage, canola, carrots, citrus and orchard tree crops, corn, cotton, cucumber, flowers and ornamentals, garlic, grapes, hops, horticultural plants, leek, melon, oil palm, onion, peanuts and legumes, pineapple, poplar, pine and wood-bearing trees, potato, raspberry, rice, sesame, sorghum, soybean, squash, strawberry, sugarcane, sunflower, tomato, turf and forage grasses, watermelon, wheat, and eucalyptus.

EXAMPLES

The following examples are provided to illustrate certain particular features and/or embodiments. These examples should not be construed to limit the disclosure to the particular features or embodiments described.

Example 1

Preparation of a Microbial Mixture for Formulation with Polymer Coating

Twenty-two bacterial strains (Agrinos Microbial Collection (AMC); described in International App. No. PCT/US2017/049326, filed Aug. 30, 2017 and incorporated herein by reference) were selected for production of microbial coated dry urea granules. The strains were either grown individually or in microbial consortia amplified in 1.5 L bench top fermenters. The strains and their growth conditions and media for individual culture are shown in Table 1.

TABLE 1

List of microorganisms used in dry fertilizer coating trial, optimal respiration and growth media options

| Microorganisms | Optimal Respiration | Growth media: individual culture |
|---|---|---|
| *Acetobacter pasteurianus* | Aerobic | YPD, MP, M-HYTA |
| *Azotobacter vinelandii* | Aerobic | RhX, MP, M-HYTA, |

TABLE 1-continued

List of microorganisms used in dry fertilizer coating trial, optimal respiration and growth media options

| Microorganisms | Optimal Respiration | Growth media: individual culture |
|---|---|---|
| *Bacillus amyloliquefaciens* | Aerobic | YPD, MP, YPDS, M-HYTA |
| *Bacillus flexus* | Aerobic | BHI, MP, M-HYTA, NA, YPD |
| *Bacillus licheniformis* | Aerobic | BHI, MP, M-HYTA |
| *Bacillus megaterium* | Aerobic | YPD, MP, YPDS, M-HYTA |
| *Bacillus* sp. | Aerobic | BHI, MP, M-HYTA, YPD |
| *Bacillus subtilis* | Aerobic | BHI, MP, M-HYTA, YPD |
| *Clostridium beijerinckii* | Anaerobic | RCM, MP, M-HYTA |
| *Clostridium pasteurianum* | Anaerobic | RCM, MP, M-HYTA, |
| *Lactobacillus buchneri* | Anaerobic | RCM, MRS, MP, M-HYTA |
| *Lactobacillus casei/paracasei* | Anaerobic | RCM, MRS, MP, M-HYTA |
| *Lactobacillus delbrueckii* | Anaerobic | RCM, MRS, MP, M-HYTA |
| *Lactobacillus vini* | Anaerobic | RCM, MRS, MP, M-HYTA |
| *Oceanobacillus oncorhynchi* | Aerobic | BHI, MP, BHIS, M-HYTA |
| *Paenibacillus chibensis* | Aerobic | BHI, MP, M-HYTA, |
| *Paenibacillus cookii* | Aerobic | BHI, MP, M-HYTA |
| *Paenibacillus lautus* | Aerobic | BHI, MP, M-HYTA |
| *Pseudomonas putida* | Aerobic | YPD, MP, YPDS, M-HYTA |
| *Pseudomonas* sp. | Aerobic | YPD, MP, YPDS, M-HYTA |
| *Streptomyces griseus* | Aerobic | YPD, MP, YPDS, M-HYTA |
| *Virgibacillus halophilus* | Aerobic | BHI, MP, BHIS, M-HYTA, YPD |

YPD: yeast peptone dextrose (BD #242720),
YPDS: YPD + 10 g/L NaCl,
RCM: reinforce *clostridium* medium (BD#218081),
BHI: Brain Heart Infusion Broth (HiMedia, # LQ077),
BHIS: BHI + 45 g/L NaCl,
RhX: ATCC Medium: 111 *Rhizobium* X Medium,
MRS: Lactobacilli MRS (BD# 288210).

Cultivation of individual strains: Each isolate from AMC was first plated on semi-solid medium from a frozen working cell bank stock. An individual colony was selected and used to inoculate 1-250 mL scale cultures with fresh sterile medium. Anaerobic/facultative anaerobic bacteria were cultured in serum bottles (Wheaton) containing 75-100 mL of the appropriate oxygen-free medium under $N_2$ gas at 30-35° C. in static incubators. Aerobic bacteria were cultured in culture tubes or flasks at 25-30° C. under constant agitation at 200-500 rpm. Incubation time varied between 24-72 hours depending on the growth rate of each strain. Upon completion, all stains were pooled into a single flask and stored at room temperature until use in dry fertilizer formulations. Additionally, a portion of the consortium was processed for freeze-dried formulations.

Freeze-dried microbial formulations were produced by mixing the liquid microbial consortia with mannitol/lyoprotectant solution (OPS Diagnostics Lebanon, N.J., USA) as per manufacturer's recommendation and the microbial suspension was aliquoted into lyophilization vials (OPS Diagnostics, Lebanon, N.J., USA). After 60 minutes at −80° C., the mixtures were placed in the FreeZone 6 freeze dry system (Labconco, Kansas City, Mo.), vacuum was applied, and the water in the samples was allowed to sublimate. Samples were stored at 4° C. until needed. In some experiments, the lyoprotectant solution was prepared by adding the following chemicals to microbial cultures for a final concentration of 0.75 g/L Tryptic Soy Broth (Becton, Dickinson and Company, USA), 10 g/L sucrose (Sigma Aldrich, USA), and 5 g/L skim milk (Carnation, Nestlé S.A, CH).

Production of co-cultivated microbial consortia by fermentation: Both aerobic and/or anaerobic bacteria were cultured in medium containing 2% molasses supplemented with essential elements such as phosphates, sodium, potassium and chlorides (in the form of commercially available Phosphate Buffer Saline) as well as amino acids, nitrogen and peptides/proteins in the form of food grade Whey powder (0.1% w/v) and non-GMO soybean extract produced enzymatically (0.25% w/v; Ferti-Nitro Plus Plant N; Ferti-Organic, Brownsville, Tex. USA). Sodium chloride concentrations ranged up to 3.5% w/v. Strains from the AMC described above were inoculated into 2 liter DASGIP bioreactors (Eppendorf North America Hauppauge, N.Y.) with a 1.5 liter working volume at a final inoculation OD600 for each strain ranging between 6.67E-05 to 6.67E-04. Ammonium hydroxide and phosphoric acid were used as base and acid solutions respectively to maintain pH between pH 5.5 and 6.9. Temperature was controlled between 28° C. and 35° C. Anaerobic fermentations were continuously sparged with $N_2$ gas to maintain an anaerobic environment while sparged air was used in aerobic fermentations as a source of oxygen for the microbes during the length of fermentation (typically up to 3 days). After fermentation, anaerobic and aerobic fermentates were pooled to generate one complete mixture of 22 strains. A typical result illustrating the number of cells per mL per strain (see below) is summarized in Table 2. Microbial content in fermentates was determined by Droplet Digital PCR (ddPCR) using Supermix For Probes (BioRAD, Hercules, Calif.), as described in International App. No. PCT/US2017/049326, filed Aug. 30, 2017 (incorporated herein by reference).

TABLE 2

Typical number of bacteria cells per mL of final liquid formulation prior to formulation with dry urea fertilizer

| Microorganisms | Number of bacteria cells per mL of final liquid microbial formulation |
|---|---|
| *B. megaterium* | 1.40E+04 |
| *L. casei/paracasei* | 9.60E+05 |
| *C. beijerinckii* | 1.60E+07 |
| *A. pasteurianus* | 1.20E+07 |
| *L. buchneri* | 1.00E+05 |
| *B. subtilis* | 1.30E+06 |
| *P. cookii* | 6.60E+03 |
| *L. vini* | 8.20E+04 |
| *B. licheniformis* | 9.30E+05 |
| *P. lautus* | 2.00E+09 |
| *O. oncorhynchi* | 2.00E+09 |
| *B. amyloliquefaciens* | 6.00E+05 |
| *Bacillus* sp. | 3.20E+05 |
| *P. putida* | 2.30E+07 |
| *Pseudomonas* sp. | 1.20E+07 |
| *S. griseus* | 7.50E+06 |
| *P. chibensis* | 5.80E+03 |
| *B. flexus* | 6.00E+06 |
| *C. pasteurianum* | 4.80E+06 |
| *A. vinelandii* | 1.30E+07 |
| *V. halophilus* | 6.10E+06 |
| *L. delbrueckii* | 2.00E+06 |

Example 2

Co-Formulation of Microbes and Slow Release Urea Granules

Standard urea granules were coated with three successive polymer layers. Each layer was made of a polymerized polyurethane coat followed by a wax layer. Polymerization of the polyurethane mix and coating with the wax took place at 130-140° F. (54.5-65.5° C.) for 5-10 min. The microbial product described in Example 1 was added during the polymer coat-building process with the $3^{rd}$ polyurethane layer. Several ratios of microbial formulation to total mass of the granules were tested. For liquid formulations, between 0.3-3 mL of microbial product per kg of granules was tested. For dry formulation between 0.059-0.59 g of freeze-dried microbes per kg of granules were produced.

Example 3

Microbial Survival—Polyurethane Coating

Up to 1 gram of finely ground microbe-coated urea granules was suspended in sterile peptone water to a final volume of 2 mL. Serial dilutions up to $10^{-6}$ were performed using peptone water as diluent. The dilutions were subsequently plated on growth media (Table 1) and incubated aerobically and anaerobically at 30° C. and 35° C., respectively. After 1-4 days of incubation, the colonies (representing the surviving bacteria in the coated urea granules) were scraped from the plates using 1X PBS and processed for identification by Droplet Digital PCR (ddPCR) using Supermix For Probes (BioRAD, Hercules, Calif.), as described in International App. No. PCT/US2017/049326, filed Aug. 30, 2017.

Bacteria of the genus *Bacillus*, specifically *Bacillus amyloliquefaciens, Bacillus megaterium, Bacillus flexus*, and *Bacillus subtilis* appeared to be the most robust, surviving the heat shock and chemicals used to build the polyurethane slow release coat over the urea granules. Moreover, survivability of these four strains was independent of whether or not they originated from a freeze-dried consortium or a liquid fermentate, even after 4 months. Other strains such as *Bacillus licheniformis, Lactobacillus delbrueckii. Paenibacillus chibensis*, and *Paenibacillus cookii* showed preference for being in a freeze-dried state for optimal survivability prior to formulation with the polyurethane (Table 3). Other strains that preferred being in a freeze-dried form prior to dry fertilizer formulation include *L. casei/paracasei and P. lautus*; however, survivability was below the detection limit in samples older than 1 month. Overall, it appears that a freeze-dried formulation of the microbial consortium prior to embedding in polyurethane was better suited for supporting survivability over the liquid version.

TABLE 3

Survival of microbes within dry fertilizer polyurethane layer using 0.59 g of freeze-dried microbes or 3 mL of liquid microbes per kg granules

| | Freeze-dried microbes | | | Liquid microbes | | |
|---|---|---|---|---|---|---|
| Bacteria strains | 1 mo | 3 mo | 4 mo | 1 mo | 3 mo | 4 mo |
| *A. pasteurianus* | – | (±) | – | – | – | – |
| *A. vinelandii* | – | – | – | – | – | – |
| *B. amyloliquefaciens* | (+) | (+) | (+) | (+) | (+) | (+) |
| *B. flexus* | (+) | (+) | (+) | (+) | (+) | (+) |
| *B. licheniformis* | (+) | (+) | (+) | – | – | – |
| *B. megaterium* | (+) | (+) | (+) | (+) | (+) | (+) |
| *B. subtilis* | (+) | (+) | (+) | (+) | (+) | (+) |
| *Bacillus* sp. | – | – | – | –* | –* | (+) |
| *C. beijerinckii* | – | – | – | – | – | – |
| *C. pasteurianum* | – | – | – | – | – | – |
| *L. buchneri* | – | – | – | – | – | – |
| *L. casei/paracasei* | (+) | – | – | – | – | – |
| *L. delbrueckii* | (+) | (+) | (+) | – | – | – |
| *L. vini* | – | – | – | – | – | – |
| *O. oncorhynchi* | – | – | – | (±) | – | – |
| *P. chibensis* | (+) | (±) | (+) | – | – | – |
| *P. cookii* | (+) | (+) | (±) | (±) | – | – |
| *P. lautus* | (+) | – | – | (+) | – | – |

TABLE 3-continued

Survival of microbes within dry fertilizer polyurethane layer using 0.59 g of freeze-dried microbes or 3 mL of liquid microbes per kg granules

| | Freeze-dried microbes | | | Liquid microbes | | |
|---|---|---|---|---|---|---|
| Bacteria strains | 1 mo | 3 mo | 4 mo | 1 mo | 3 mo | 4 mo |
| *P. putida* | – | – | – | – | – | – |
| *Pseudomonas* sp. | – | – | – | – | – | – |
| *S. griseus* | – | – | – | – | – | – |
| *V. halophilus* | – | – | – | – | – | – |

(–) Survivability not detected;
(+) Surviving;
(±) difficult to call;
(–)* false negative

Example 4

Microbe Survivability in Different Coating Layers

In separate experiments the microbial consortium was added to different layers of the slow-release coat during the coating process: 1) over the final wax layers (after solidification of the wax that constitutes the final outer coat of the granule (FIG. 1)), 2) embedded within the final wax layer (microbes and wax were co-applied to the fertilizer granules during final coating process) and 3) sandwiched between the final wax layer and the 3rd polymer coat (microbes were added after the third polyurethane layer had cured and before the final addition of wax forming the outer coat of the granules). Microbial viability was analyzed as previously described and results are summarized in Table 4.

TABLE 4

Microbe location within the coat layers and survivability in polyurethane coated urea granules

| Microorganism | Over the final wax layer | Within the final wax layer | Between the final wax layer and the 3rd polyurethane layer |
|---|---|---|---|
| *Acetobacter pasteurianus* | – | – | – |
| *Azotobacter vinelandii* | – | – | – |
| *Bacillus amyloliquefaciens* | (+) | (+) | (+) |
| *Bacillus flexus* | – | – | – |
| *Bacillus licheniformis* | (+) | (+) | (+) |
| *Bacillus megaterium* | (+) | (+) | – |
| *Bacillus* sp. | – | – | – |
| *Bacillus subtilis* | (+) | (+) | (+) |
| *Clostridium beijerinckii* | (+) | (+) | – |
| *Clostridium pasteurianum* | – | – | – |
| *Lactobacillus buchneri* | (+) | – | (+) |
| *Lactobacillus casei/paracasei* | (+) | – | – |
| *Lactobacillus delbrueckii* | – | – | – |
| *Lactobacillus vini* | (+) | – | – |
| *Oceanobacillus oncorhynchi* | – | – | – |
| *Paenibacillus chibensis* | (+) | (+) | – |
| *Paenibacillus cookii* | (+) | (+) | – |
| *Paenibacillus lautus* | (+) | (+) | – |
| *Pseudomonas putida* | (+) | – | – |
| *Pseudomonas* sp. | (+) | – | – |
| *Streptomyces griseus* | – | – | – |
| *Virgibacillus halophilus* | – | – | – |

– Survivability not detected;
(+) Surviving

Example 5

Microbe Survival—Non-Urethane Resin Coating

In this instance, 0.59 g of freeze-dried microbes or 3 mL of liquid fermentate per kg of granules were embedded in the $3^{rd}$ polymer layer, which was a non-urethane polymer, during the coating process. Microbial survivability was determined after 1 month as described above. Results are summarized in the table below. *Bacillus amyloliquefaciens, Bacillus flexus, Bacillus megaterium, Bacillus subtilis, Lactobacillus delbrueckii, Paenibacillus chibensis, Paenibacillus cookii*, and *Paenibacillus lautus* appeared to survive the embedding process after 1 month in the coat (Table 5).

TABLE 5

Surviving microbes from liquid and freeze-dried initial formulations within the $3^{rd}$ on non-urethane resin layer of coated urea granules.

| Microorganisms | Liquid formulation | Freeze-dried formulation |
|---|---|---|
| *Acetobacter pasteurianus* | – | – |
| *Azotobacter vinelandii* | – | – |
| *Bacillus amyloliquefaciens* | (+) | (+) |
| *Bacillus flexus* | (+) | (+) |
| *Bacillus licheniformis* | – | – |
| *Bacillus megaterium* | – | (+) |
| *Bacillus* sp. | – | – |
| *Bacillus subtilis* | (+) | (+) |
| *Clostridium beijerinckii* | – | – |
| *Clostridium pasteurianum* | – | – |
| *Lactobacillus buchneri* | – | – |
| *Lactobacillus casei/paracasei* | – | – |
| *Lactobacillus delbrueckii* | – | (+) |
| *Lactobacillus vini* | – | – |
| *Oceanobacillus oncorhynchi* | – | – |
| *Paenibacillus chibensis* | – | (+) |
| *Paenibacillus cookii* | – | (+) |
| *Paenibacillus lautus* | (+) | (+) |
| *Pseudomonas putida* | – | – |
| Pseudomonas sp. | – | – |
| *Streptomyces griseus* | – | – |
| *Virgibacillus halophilus* | – | – |

– Survivability not detected;
(+) Surviving

Example 6

Identification of Microbial Metabolic Activity Potential

Salt tolerance assay: All strains in the microbial consortium demonstrated acceptable growth in laboratory-grade Yeast Peptone Dextrose medium (YPD, Difco 242820). This medium was therefore used to determine the salt tolerance of each isolate using variable amounts of sodium chloride (a standard for salt-tolerance testing) up to 5% w/v. Each isolate was cultured in 2 ml of medium under ideal growth conditions. 30° C. with agitation (125-175 rpm) of aerobes and 35° C. with no agitation for anaerobes in anaerobic chambers (BD diagnostics). At 24, 48, and 72 hrs, growth was recorded for each culture based on the general equivalence to MacFarland standards (available on the World Wide Web at pro-lab.com/inserts/McFarland.pdf). Any isolate showing growth at 5% NaCl at 72 hours was recorded as having a NaCl tolerance≥5%, growth at 2.5% is ≥2.5% and so on.

Nitrogen (N) fixation assay: Nitrogen-free semi-solid medium containing sucrose 5.0 g/L, $MgSO_4$ 0.2 g/L; $KH_2PO_4$0.8 g/L; $FeSO_4$ 0.04 g/L; $Na_2MoO_4$; 0.005 g/L, $CaCO_3$ 2 g/L and 15 g/L Agar was prepared and sterilized by autoclaving. From a master culture plate, a single colony of each isolate was transferred to a N-free plate aseptically. Using the streaking-out method, colonies were spread onto fresh N-free plates. Growth conditions varied based on the isolate: Anaerobic/microaerophilic bacteria were incubated at 35° C. in anaerobic chambers while aerobic bacteria were incubated at 30° C. Incubation times extended up to 1 week before scoring for growth. Only robust nitrogen fixers (e.g., robust growth) were scored as positive.

Calcium salt solubilization assay: Calcium carbonate semi-solid medium containing $MgSO_4$0.3/L; $CaCl_2$ 01.g/L; $FeSO_4$0.12 g/L; $K_2SO_4$1 g/L; Sucrose 20 g/L; $Na_2MoO_4$0.01 g/L; $MnCl_2$ 0.01 g/L; yeast extract 5 g/L; peptone 10 g/L; $CaCO_3$ 2 g/L; agar 15 g/L was prepared and sterilized by autoclaving. From a master culture plate, a single colony of each isolate was transferred to a carbonate plate, aseptically. A single streak was drawn down the middle of the plate. Growth conditions varied based on the isolate: Anaerobic/microaerophilic bacteria were incubated at 35° C. in anaerobic chambers while aerobic bacteria were incubated at 30° C. Incubation times extended up to 1 week before scoring for the presence of a clearing area adjacent to the bacteria. Only obvious clearing of the $CaCO_3$ precipitate was scored as positive.

Phosphate salt solubilization assay: Calcium Phosphate semi-solid medium containing $MgSO_4$0.3/L; $CaCl_2$ 01. g/L; $FeSO_4$ 0.12 g/L; $K_2SO_4$ g/L; Sucrose 20 g/L; $Na_2MoO_4$0.01 g/L; $MnCl_2$ 0.01 g/L; yeast extract 5 g/L; peptone 10 g/L; $Ca_3(PO_4)_2$ 5 g/L; agar 15 g/L was prepared and sterilized by autoclaving. From a master culture plate, a single colony of each isolate was transferred to a carbonate plate, aseptically. A single streak was drawn down the middle of the plate. Growth conditions varied based on the isolate: Anaerobic/microaerophilic bacteria were incubated at 35° C. in anaerobic chambers while aerobic bacteria were incubated at 30° C. Incubation times extended up to 1 week before scoring for the presence of a clearing area adjacent to the bacteria. Only obvious clearing of the calcium phosphate precipitate was scored as positive.

Zinc salt solubilizing assay: To test strains for the ability to solubilize zinc, four types of zinc were utilized in the assay: $Zn_5(CO_3)_2(OH)_6$ (zinc carbonate hydroxide), $Zn_3(PO_4)_2$ (zinc phosphate), ZnO (zinc oxide) and $ZnSO_4$ (zinc sulfate). Each type of zinc was then added at 0.2% (w/v) to either Brain-Heart Infusion (BHI) or YPD agar media. For each strain, a single colony was then selected and streaked out onto both semi-solid media in Petri dishes. Aerobes were incubated at 30° C. and anaerobes were incubated at 35° C. in a static incubator for 3 days. Plates were checked after 24, 48 and 72 hours for signs of clearing in the medium, which is interpreted as a positive indicator of zinc-solubilization.

Iron mobilizing analysis: A number of soil microbes produce so-called siderophores in environments with low concentrations of iron—an essential micronutrient. These compounds form water soluble complexes with $Fe^{3+}$, which can be released in situations of iron deficiency. Both bacteria siderophores benefit both plants and microbes as a localized source of iron. Whole-genome sequences analysis for each of the 22 isolates was performed focusing on the detection genes coding for the siderophores, siderophore biosynthesis pathway(s) as well as siderophore receptors and transporters such as Yus, Yfh, Yfi, Asb, Fur, TonB, ExbB, ExbD, Citrate, Desferrioxamine, Deferoxamine, Ferrichrome, Fusarinine, Ornibactin, Chrysobactin, Vibriobactin, Mycobactin, Pyoverdin, Pyochelin, Yersiniabactin, Enterobactin, Achromobactin, Acinetobactin, Azotobactin, Bacillibactin, and Anguibactin. This enabled determination of whether not a given microbe possessed the metabolic arsenal to perform to produce and/or transport iron mobilizing compounds.

Analysis of microbial organic matter dephosphorylation potential: Bacteria can release a range of microbial enzymes which through there action on organic matter, can produce phosphate forms accessible by plants. These enzymes include non-specific phosphatases that dephosphorylate phosphoester and/or phosphoanhydride bonds in organic matter, phytases that release phosphorus from phytic acid and phosphonatases and C—P lyases that dissociate C—P bonds in organophosphonates. Whole-genome sequence analysis for each of the 22 isolates was performed focusing on the detection genes coding for these enzymes in functional metabolic pathways. This enabled determination of whether not a given microbe possessed the enzymatic arsenal to perform the dephosphorylation of organic matter in the soil.

Chitinase assay: Colloidal chitin plate assays were performed essentially as described by Hsu and Lockwood (*Applied Microbiology,* 29:422-426, 1975). Bacteria colonies (1-3 days old) picked from master plates were streaked on colloidal chitin plates (semi-dry chitin, 5 g/L; $K_2HPO_4$, 0.7 g/L; $KH_2PO_4$, 0.3 g/L; $MgSO_4.5H_2O$, 0.5 g/L; $FeSO_4.7H_2O$, 0.01 g/L; $ZnSO_4$, 0.001 g/L; $MnCl_2$, 0.001 g/L and agar, 15 g/L). Plates were incubated at 30° C. for aerobes, 35° C. under anaerobic conditions for anaerobes for up to 1 week. Chitinase positive isolates were identified by clearing in the medium and/or significant microbial growth.

Cellulase assay: The Deoxymethyl Cellulose Plate Assay was adapted from Alves et al. (*The Open Microbiology Journal,* 8:25-31, 2014). In brief, bacteria colonies (1-3 days old) picked from master plates were streaked on semi-solid medium (Deoxymethyl cellulose, 0.5% w/v; agarose 1.5% w/v; Tris-HCl, 50 mM pH 6.8; $CaCl_2$, mM). Bacteria isolates were subsequently incubated at 30° C. for aerobes, 35° C. under anaerobic conditions for anaerobes for up to 1 week. Each plate was subsequently treated with a solution of Congo Red (0.25% w/v in 0.1M Tris-HCl pH 8.0) and destained with NaCl 0.5% w/v in 0.1 M Tris-HCl, pH 8.0. Cellulase positive isolates were identified by clearing in the medium and/or significant microbial growth.

Indole-3-acetic acid (IAA) production assay: IAA assay was conducted on each microbial isolate grown in liquid media supplemented with 1-5 mg/mL of Tryptophan. Seven to fourteen days post inoculation, the cultures were tested for IAA production using Salkowski's reagent as described in Glickmann et al. (*Applied and Environmental Microbiology*, February 1995, p 793-796). Briefly, clarified spent medium from each culture was mixed with Salkwoski's reagent at a ratio of 1:1. After 30 min incubation, the absorbance at 540 nm was measured. Assessment of IAA production was conducted using a previously prepared standard curve using purified IAA (Alfa-Aesar, Tewksbury, Mass. USA). In addition, whole-genome sequence analysis for each of the 22 isolates was performed focusing on the detection the auxin biosynthesis pathways.

Other metabolic assays: For additional metabolic activities including denitrification assays, urease production, and malic acid assimilation, bioMérieux's API® identification products were used according to the manufacturer's recommendations (bioMérieux, Inc., Durham, N.C. USA).

Analysis of the microbial functionalities retained in the surviving microbes at 1 months and 4 months post formulation showed that the key plant/soil beneficial functionalities attributed to the microbes forming the initial consortium (Table 1) were still well represented in the microbes surviving in polyurethane-coated urea granules (Table 6). The freeze-dried formulations of microbes gave a greater diversity in plant beneficial microbial functionalities over the liquid formulation. This is in line with the previous observation showing higher number of bacteria species surviving the dry fertilizer formulations when originating from freeze-dried microbial material. All key plant beneficial functionalities from the original consortium in Table 1 were represented, many with redundancy (Table 7).

TABLE 6

Summary of metabolic activities of surviving microbes in polyurethane coated urea granules.

| | | Polyurethane coated urea granules (1 month) | | Polyurethane coated urea granules (4 months) | |
|---|---|---|---|---|---|
| Surviving microbial functionalities | Initial consortium | Liquid formulation | Freeze-dried formulation | Liquid formulation | Freeze-dried formulation |
| Nitrogen metabolism | 13 - D<br>10 - N<br>1 - U | 5 - D<br>5 - N<br>0 - U | 6 - D<br>6 - N<br>0 - U | 3 - D<br>4 - N<br>0 - U | 5 - D<br>6 - N<br>0 - U |
| Salt tolerant | 13 - ≥5%<br>08 - <5%<br>01 - <1% | 5 - ≥5%<br>1 - <5% | 7 - ≥5%<br>3 - <5% | 5 - ≥5%<br>0 - <5% | 5 - ≥5%<br>3 - <5% |
| Mineral solubilization | 7 - P<br>7 - Ca<br>6 - Zn | 1 - P<br>1 - Ca<br>0 - Zn | 3 - P<br>3 - Ca<br>2 - Zn | 0 - P<br>0 - Ca<br>0 - Zn | 1 - P<br>1 - Ca<br>1 - Zn |
| Cellulolytic/ chitinolytic | 4 - Cellulolytic<br>3 - Chitinolytic | 3 - Cellulolytic<br>1 - Chitinolytic | 3 - Cellulolytic<br>2 - Chitinolytic | 3 - Cellulolytic<br>0 - Chitinolytic | 3 - Cellulolytic<br>0 - Chitinolytic |
| Other Plant Beneficial Activity | 14 - IAA<br>12 - M | 4 - IAA<br>6 - M | 7 - IAA<br>8 - M | 3 - IAA<br>4 - M | 6 - IAA<br>7 - M |
| Sulfur metabolism | 2 | 2 | 2 | 2 | 2 |
| De-phosphorylation of organic matter | 22 | 6 | 10 | 4 | 8 |

TABLE 6-continued

Summary of metabolic activities of surviving microbes in polyurethane coated urea granules.

| | | Polyurethane coated urea granules (1 month) | | Polyurethane coated urea granules (4 months) | |
|---|---|---|---|---|---|
| Surviving microbial functionalities | Initial consortium | Liquid formulation | Freeze-dried formulation | Liquid formulation | Freeze-dried formulation |
| Iron mobilization/ Siderophores | 17 | 6 | 8 | 4 | 7 |
| Anaerobic respiration | 6 | 0 | 2 | 0 | 1 |
| Aerobic respiration | 16 | 6 | 8 | 4 | 7 |

D: denitrification,
N: Nitrogen fixation,
U: urease activity,
P: phosphate,
Ca: calcium,
Zn: zinc,
IAA: Indole-3-acetic acid production,
M: Malic acid assimilation,
(+): metabolic pathway detected through whole genome sequence analysis.

TABLE 7

Surviving microbes and associated functionalities from freeze-dried microbial formulation in polyurethane coated urea granules after 4 months.

| | Plant beneficial microbial functionalities | | | | | | | |
|---|---|---|---|---|---|---|---|---|
| Microbes | Nitrogen metab. | Salt tolerant | Mineral solub. | Cellulolytic/ chitinolytic | Other Plant Beneficial Activity | Sulfur metab. | De-phospho-rylation of organic matter | Iron mob./ Siderophores |
| *Bacillus amyloliquefaciens* | D, N | ≥5% | | Cellulose | M + IAA | | (+) | (+) |
| *Bacillus flexus* | N | ≥5% | | Cellulose | M + IAA | Can use $Na_2SO_4$ as only S source | (+) | (+) |
| *Bacillus licheniformis* | D, N | ≥5% | | Chitin | M + IAA | | (+) | (+) |
| *Bacillus megaterium* | D, N | ≥5% | | | M | Can use Na2SO4 as only S source | (+) | (+) |
| *Bacillus subtilis* | D, N | ≥5% | | Cellulose | M + IAA | | (+) | (+) |
| *Lactobacillus delbrueckii* | | ≤2.5% | P, Ca, Zn | | | | (+) | |
| *Paenibacillus chibensis* | | <5% | | | M + IAA | | (+) | (+) |
| *Paenibacillus cookii* | D, N | ≤2.5% | | | M + IAA | | (+) | (+) |

D: denitrification,
N: Nitrogen fixation,
U: urease activity
P: phosphate,
Ca: calcium,
Zn: zinc,
IAA: Indole-3-acetic acid production,
M: Malic acid assimilation,
(+): metabolic pathway detected through whole genome sequence analysis.

Example 7

Evaluation of Plant Growth Promoting Activity

Figure 2:
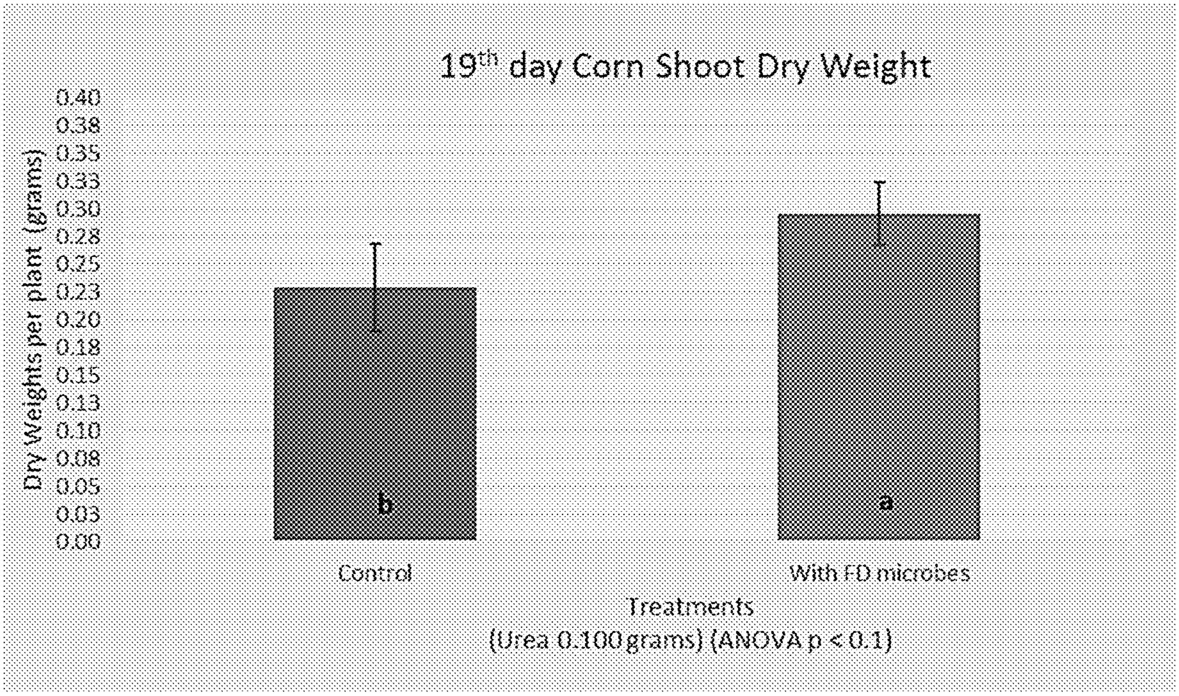
FIG. 2 is a graph showing day 19 corn shoot dry weight. Treatments were polyurethane coated urea granules (Control, n=8) or polyurethane plus freeze-dried microbes in urea granules (with FD microbes, n=9).

Corn seeds (Alberta Lea Seeds, Albert Lea, Minn.) were soaked in water for 4 hours at room temperature before planting in potting soil or soilless growth medium (Sunshine Mix) pre-treated with a Modified Hoagland (Hoagland, *Calif. Agric. Exp. Stn. Bull.* 347:36-39, 1938) solution (P, 30.97 ppm; K, 39.1 ppm; Ca, 40.0 ppm; Mg, 14.59 ppm; S, 20.143 ppm; Fe, 1.010 ppm; Cu, 0.019 ppm; Co, 0.012 ppm; B, 2.44 ppm; Mn, 0.494 ppm; Mo, 0.001 ppm and Zn, 0.056 ppm) and 1:1,000 dilution of AMC product described in Example 1. At seed planting, 100 mg of polyurethane coated slow release urea fertilizer (control) or polyurethane/microbe coated slow release urea fertilizer (described in Example 2) was added to the soil. Trays with 8 to 9 pots were incubated in the dark for 3 days at 25° C. in a temperature and humidity controlled growth chamber (Sheldon Manufacturing, Inc. Cornelius, Oreg.). The plants were then grown for 16-20 days in growth room conditions of 16-24° C. and 12 hours photoperiod. Watering was performed 3 times per week with modified Hoagland solution. Dry shoot weights were subsequently determined after 4 days of drying at 75° C. (FIG. 2). Data was analyzed by One-way ANOVA (Analysis Of Variance).

Example 8

Production of Microbial Dry Fertilizer

*Bacillus amyloliquefaciens, Bacillus flexus, Bacillus megaterium, Bacillus subtilis, Bacillus licheniformis*, and *Lactobacillus delbrueckii* are grown in medium containing 2-6% w/v molasses, 0.1% w/v whey powder, 0.25% w/v Ferti Nitro Plus, 0.8% NaCl and 0.1% $K_2HPO_4$. The microbes are cultured individually or in co-culture to produce a final consortium of six microbes. Using digital PCR as previously described, the number of cells for each strain in the respective consortia is determined. A portion of each consortium is freeze-dried (as described above) and both liquid and freeze-dried consortia are used in co-formulation with polyurethane to coat urea granules. In these studies, up to 3 mL (liquid microbe formulation) or 0.59 g (freeze-dried) of microbes per kg of urea granules is used.

Example 9

Production of Fertilizer With Microbes Between Layers

In some embodiments, the fertilizer composition includes a microbial composition that is coated between layers on the fertilizer granule. Conditions for forming the layers can be those provided in Example 2. An exemplary sequence of coating includes:

1. Fertilizer is weighed into mixer
2. Layer 1—Polyol is charged to mixer
3. Preset mixing time
4. Layer 1—MDI is charged to mixer
5. Preset mixing time
6. Wax is charged to mixer
7. Preset mixing time
8. Coating steps are repeated until targeted coating level is achieved.

The microbes can be added after any one of steps 2, 4, or 6, so that they are present between polymer and wax layers.

In addition to, or as an alternative to the above, the following embodiments are described:

Embodiment 1 is directed to a composition comprising a core particle comprising at least one fertilizer nutrient; and a shell substantially covering the core particle, wherein the shell comprises at least one polymer layer or wax layer and one or more species of microbes.

Embodiment 2 is directed to the composition of embodiment 1, wherein the polymer layer and/or the wax layer comprises the one or more species of microbes.

Embodiment 3 is directed to the composition of embodiment 1, wherein the one or more species or microbes are between two polymer layers, between two wax layers, and/or between a polymer layer and a wax layer.

Embodiment 4 is directed to the composition of embodiment 1, comprising two or more polymer and/or wax layers, wherein at least one of the polymer layers and/or at least one of the wax layers comprises the one or more species of microbes.

Embodiment 5 is directed to the composition of any one of embodiments 2 to 4, wherein the composition comprises a layer of wax between two or more polymer layers.

Embodiment 6 is directed to the composition of any one of embodiments 1 to 5, wherein the outer layer comprises the one or more species of microbes.

Embodiment 7 is directed to the composition of any one of embodiments 1 to 6, wherein the at least one fertilizer nutrient is selected from an N—P—K fertilizer.

Embodiment 8 is directed to the composition of embodiment 7, wherein the N comprises urea, ammonium nitrate, or a combination thereof.

Embodiment 9 is directed to the composition of any one of embodiments 1 to 8, wherein the core particle is a urea granule.

Embodiment 10 is directed to the composition of any one of embodiments 1 to 9, wherein the polymer comprises polyurethane.

Embodiment 11 is directed to the composition of any one of embodiments 1 to 10, wherein the one or more species of microbes have nitrogen metabolism activity; salt tolerance; phosphorus, calcium, and/or zinc solubilization activity; cellulolytic and/or chitinolytic activity; malic acid assimilation activity; indole-3-acetic acid production activity; sulfur metabolism activity; dephosphorylation of organic matter activity; iron mobilization/siderophore activity; or a combination of two or more thereof.

Embodiment 12 is directed to the composition of any one of embodiments 1 to 11, wherein the one or more species of microbes are selected from *Lactobacillus delbrueckii, Virgibacillus halophilus, Azotobacter vinelandii, Clostridium pasteurianum, Paenibacillus chibensis, Streptomyces griseus, Pseudomonas sp* (closely related to *P. entomophila, P. fluorescens*, and *P. putida*, for example, a microbial species with 16S rRNA sequence with at least 99% sequence identity to SEQ ID NO: 17), *Pseudomonas putida, Bacillus sp* (closely related to *B. kochii, B. pocheonensis*, and *Bacillus sp* (strain R-27341), for example, a microbial species with a 16S rRNA sequence with at least 99% sequence identity to SEQ ID NO: 15), *Bacillus amyloliquefaciens, Oceanobacillus oncorhynchi, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*.

Embodiment 13 is directed to the composition of embodiment 12, wherein the one or more species of microbes have 16S rDNA sequences having at least 99% sequence identity to one of SEQ ID NOs: 1-22.

Embodiment 14 is directed to the composition of any one of embodiments 1 to 11, wherein the one or more species of microbes comprise *Bacillus amyloliquefaciens, Bacillus flexus, Bacillus licheniformis, Bacillus megaterium, Bacillus subtilis, Lactobacillus delbrueckii, Paenibacillus chibensis*, and/or *Paenibacillus cookii*.

Embodiment 15 is directed to the composition of embodiment 14, wherein the one or more species of microbes have 16S rDNA sequences having at least 99% sequence identity to one of SEQ ID NOs: 1, 6, 7, 9, 12, 17, 18, and 22.

Embodiment 16 is directed to the composition of any one of embodiments 1 to 11, wherein the one or more species of microbes comprise *Bacillus amyloliquefaciens, Bacillus flexus, Bacillus licheniformis, Bacillus megaterium, Bacillus subtilis*, and/or *Lactobacillus delbrueckii*.

Embodiment 17 is directed to the composition of embodiment 16, wherein the one or more species of microbes have 16S rDNA sequences having at least 99% sequence identity to one of SEQ ID NOs: 1, 6, 9, 12, 17, and 22.

Embodiment 18 is directed to a method of making a fertilizer-microbial composition, comprising: (i) contacting a core particle comprising at least one fertilizer nutrient with a mixture comprising a polymer, pre-polymer, or oligomer and one or more species of microbes to form a layer substantially covering the core particle; and polymerizing the polymer, pre-polymer, or oligomer to form a coated core particle; and/or (ii) contacting a core particle comprising at least one fertilizer nutrient with a mixture comprising wax and one or more species of microbes to form a layer substantially covering the core particle.

Embodiment 19 is directed to a method of making a fertilizer-microbial composition, comprising: (i) contacting a core particle comprising at least one fertilizer nutrient with a mixture comprising a polymer, pre-polymer, or oligomer; and polymerizing the polymer, pre-polymer, or oligomer to form a polymer layer; (ii) contacting the core particle comprising at least one fertilizer nutrient with wax to form a wax layer; and/or (iii) contacting the core particle comprising at least one fertilizer nutrient with one or more species of microbes to form a layer of microbes, wherein steps (i)-(iii) may be performed in any order and/or repeated one or more times.

Embodiment 20 is directed to the method of any one of embodiments 18 or 19, wherein outer layer comprises the one or more species of microbes.

Embodiment 21 is directed to the method of any one of embodiments 18 to 20, wherein the at least one fertilizer nutrient is selected from an N—P—K fertilizer.

Embodiment 22 is directed to the method of embodiment 21, wherein the N comprises urea, ammonium nitrate, or a combination thereof.

Embodiment 23 is directed to the method of any one of embodiments 18 to 22, wherein the core particle is a urea granule.

Embodiment 24 is directed to the method of any one of embodiments 18 to 23, wherein the polymer comprises polyurethane.

Embodiment 25 is directed to the method of any one of embodiments 18 to 24, wherein the one or more species of microbes are in a liquid form.

Embodiment 26 is directed to the method of any one of embodiments 18 to 24, wherein the one or more species of microbes are in a freeze-dried form.

Embodiment 27 is directed to the method of any one of embodiments 18 to 26, wherein the one or more species of microbes have nitrogen metabolism activity; salt tolerance; phosphate, calcium, and/or zinc solubilization activity; cellulolytic and/or chitinolytic activity; malic acid assimilation activity; indole-3-acetic acid production activity; sulfur metabolism activity; dephosphorylation of organic phosphate activity; iron mobilization/siderophore activity; or a combination of two or more thereof.

Embodiment 28 is directed to the method of any one of embodiments 18 to 27, wherein the one or more species of microbes are selected from *Lactobacillus delbrueckii, Virgibacillus halophilus, Azotobacter vinelandii, Clostridium pasteurianum, Paenibacillus chibensis, Streptomyces griseus, Pseudomonas sp* (closely related to *P. entomophila, P. fluorescens*, and *P. putida*, for example, a microbial species with 16S rRNA sequence with at least 99% sequence identity to SEQ ID NO: 17), *Pseudomonas putida, Bacillus sp* (closely related to *B. kochii, B. pocheonensis*, and *Bacillus sp* (strain R-27341), for example, a microbial species with a 16S rRNA sequence with at least 99% sequence identity to SEQ ID NO: 15), *Bacillus amyloliquefaciens, Oceanobacillus oncorhynchi, Paenibacillus lautus* (e.g., closely related to *Paenibacillus lautus* and *Paenibacillus sp* (strain Y412MC10), for example, a microbial species with 16S rRNA sequence with at least 99% sequence identity to SEQ ID NO: 12), *Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus*.

Embodiment 29 is directed to the method of embodiment 28, wherein the one or more species of microbes have 16S rDNA sequences having at least 99% sequence identity to one of SEQ ID NOs: 1-22.

Embodiment 30 is directed to the method of any one of embodiments 18 to 27, wherein the one or more species of microbes comprise American Type Culture Collection deposit number PTA-123288, PTA-123298, PTA-123289, or a combination of two or more thereof.

Embodiment 31 is directed to the method of any one of embodiments 18 to 27, wherein the one or more species of microbes comprise *Bacillus amyloliquefaciens, Bacillus flexus, Bacillus licheniformis, Bacillus megaterium, Bacillus subtilis, Lactobacillus delbrueckii, Paenibacillus chibensis*, and/or *Paenibacillus cookii*.

Embodiment 32 is directed to the method of embodiment 31, wherein the one or more species of microbes have 16S rDNA sequences having at least 99% sequence identity to one of SEQ ID NOs: 1, 6, 7, 9, 12, 17, 18, and 22.

Embodiment 33 is directed to the method of any one of embodiments 18 to 27, wherein the one or more species of microbes comprise *Bacillus amyloliquefaciens, Bacillus flexus, Bacillus licheniformis, Bacillus megaterium, Bacillus subtilis*, and/or *Lactobacillus delbrueckii*.

Embodiment 34 is directed to the method of embodiment 33, wherein the one or more species of microbes have 16S rDNA sequences having at least 99% sequence identity to one of SEQ ID NOs: 1, 6, 9, 12, 18, and 22.

Embodiment 35 is directed to a fertilizer-microbial composition made by the method of any one of embodiments 18 to 34.

Embodiment 36 is directed to a method comprising contacting soil, plants, plant parts, or seeds with the composition of any one of embodiments 1 to 17.

Embodiment 37 is directed to the method of embodiment 36, comprising contacting soil with the composition to produce treated soil and cultivating seeds, seedlings, or plants in the treated soil.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A composition comprising:

a core particle comprising at least one fertilizer nutrient; and a shell substantially covering the core particle, wherein the shell comprises at least one polymer layer comprising polyurethane and one or more species of microbes.

2. The composition of claim 1, comprising two or more polyurethane and/or wax layers, wherein at least one of the polyurethane layers comprises the one or more species of microbes.

3. The composition of claim 2, wherein the composition comprises a layer of wax between two or more polyurethane layers.

4. The composition of claim 1, wherein the one or more species of microbes comprise each of *Lactobacillus delbrueckii, Virgibacillus halophilus, Azotobacter vinelandii, Clostridium pasteurianum, Paenibacillus chibensis, Streptomyces griseus, Pseudomonas sp Pseudomonas putida, Bacillus sp Bacillus amyloliquefaciens, Oceanobacillus oncorhynchi, Paenibacillus lautus Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus.*

5. The composition of claim 4, wherein each of the one or more species of microbes have 16S rDNA sequences having at least 99% sequence identity to one of SEQ ID NOs: 1-22.

6. The composition of claim 1, wherein the outer layer comprises the one or more species of microbes.

7. The composition of claim 1, wherein the at least one fertilizer nutrient is urea, monoammonium phosphate, diammonium phosphate, ammonium nitrate, potassium nitrate, potassium sulfate, or ammonium sulfate.

8. A method of making a fertilizer-microbial composition, comprising:

contacting a core particle comprising at least one fertilizer nutrient with a mixture comprising a polyol and a diisocyanate and one or more species of microbes to form a layer substantially covering the core particle; and polymerizing the polyol and diisocyanate to form a polyurethane coated core particle, wherein the polyurethane coating comprises the one or more species of microbes.

9. The method of claim 8, wherein the one or more species of microbes comprise each of *Lactobacillus delbrueckii, Virgibacillus halophilus, Azotobacter vinelandii, Clostridium pasteurianum, Paenibacillus chibensis, Streptomyces griseus, Pseudomonas sp. Pseudomonas putida, Bacillus sp. Bacillus amyloliquefaciens, Oceanobacillus oncorhynchi, Paenibacillus lautus Bacillus licheniformis, Lactobacillus vini, Paenibacillus cookii, Bacillus subtilis, Lactobacillus buchneri, Bacillus megaterium, Acetobacter pasteurianus, Clostridium beijerinckii, Lactobacillus casei/paracasei*, and *Bacillus flexus.*

10. The method of claim 9, wherein the each of the one or more species of microbes have 16S rDNA sequences having at least 99% sequence identity to one of SEQ ID NOs: 1-22.

11. The method of claim 8, wherein the at least one fertilizer nutrient is urea, monoammonium phosphate, diammonium phosphate, ammonium nitrate, potassium nitrate, potassium sulfate, or ammonium sulfate.

12. The method of claim 8, wherein the one or more species of microbes are in a liquid form.

13. The method of claim 8, wherein the one or more species of microbes are in a freeze-dried form.

14. The method of claim 8, wherein the one or more species of microbes comprise American Type Culture Collection deposit number PTA-123288, PTA-123298, PTA-123289, or a combination of two or more thereof.

15. The method of claim 8, wherein the diisocyanate is methylene diphenyl diisocyanate (MDI) or toluene diisocyanate (TDI).

16. A fertilizer-microbial composition made by the method of claim 8.

17. A method of making a fertilizer-microbial composition, comprising:

(i) contacting a core particle comprising at least one fertilizer nutrient with a mixture comprising a polyol and a diisocyanate and one or more species of microbe; and polymerizing the polyol and diisocyanate to form a polyurethane layer comprising the one or more species of microbes; and (ii) contacting the core particle comprising at least one fertilizer nutrient with wax to form a wax layer;

wherein steps (i) and (ii) may be performed in either order and/or repeated one or more times.

18. The method of claim 17, wherein outer layer comprises the one or more species of microbes.

19. The method of claim 17, wherein the diisocyanate is methylene diphenyl diisocyanate (MDI) or toluene diisocyanate (TDI).

20. A method comprising contacting soil, plants, plant parts, or seeds with the composition of claim 1.

* * * * *